US012758381B2

(12) United States Patent
Eidenschink et al.

(10) Patent No.: US 12,758,381 B2
(45) Date of Patent: Oct. 13, 2026

(54) CUFF TECHNOLOGIES FOR BALLOON EXPANDABLE VALVES

(71) Applicant: St. Jude Medical, Cardiology Division, Inc., St. Paul, MN (US)

(72) Inventors: Tracee Eidenschink, Wayzata, MN (US); Peter J. Ness, Minneapolis, MN (US); Tyler Govek, Minneapolis, MN (US); Brandon Moore, St. Louis Park, MN (US); Jay Reimer, Shoreview, MN (US); Prem Midha, St. Paul, MN (US); Nick Tulshibagwale, Santa Barbara, CA (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 556 days.

(21) Appl. No.: 18/353,312

(22) Filed: Jul. 17, 2023

(65) Prior Publication Data

US 2024/0041594 A1 Feb. 8, 2024

Related U.S. Application Data

(60) Provisional application No. 63/370,380, filed on Aug. 4, 2022.

(51) Int. Cl.
*A61F 2/24* (2006.01)

(52) U.S. Cl.
CPC .................................. *A61F 2/2415* (2013.01)

(58) Field of Classification Search
CPC ......... A61F 2/24; A61F 2/2415; A61F 2/2418
See application file for complete search history.

(56) References Cited

U.S. PATENT DOCUMENTS

| | | | | |
|---|---|---|---|---|
| 8,454,685 B2 | 6/2013 | Hariton | | |
| 8,808,356 B2 | 8/2014 | Braido | | |
| 9,326,856 B2 | 5/2016 | Schraut | | |
| 10,548,722 B2 | 2/2020 | Morin | | |
| 2006/0259136 A1* | 11/2006 | Nguyen | A61F 2/2412 | 623/2.18 |
| 2012/0123529 A1* | 5/2012 | Levi | A61F 2/2418 | 623/2.11 |
| 2013/0144382 A1* | 6/2013 | DeStefano | A61F 2/2418 | 112/475.08 |
| 2015/0320556 A1* | 11/2015 | Levi | A61F 2/2418 | 29/515 |
| 2018/0104052 A1 | 4/2018 | Salahieh | | |
| 2022/0096225 A1 | 3/2022 | Braido | | |

FOREIGN PATENT DOCUMENTS

WO 2019194956 10/2019

* cited by examiner

*Primary Examiner* — Tuan V Nguyen
(74) *Attorney, Agent, or Firm* — SLEMAN & LUND LLP

(57) ABSTRACT

A method of manufacturing a prosthetic heart valve includes coupling a plurality of prosthetic leaflets to each other, and coupling the plurality of prosthetic leaflets to a cuff, to form a valve assembly. The valve assembly may be coupled to a stent to form the prosthetic heart valve. The valve assembly may be formed prior to the plurality of prosthetic leaflets being coupled to the stent and prior to the cuff being coupled to the stent.

7 Claims, 15 Drawing Sheets

CUFF TECHNOLOGIES FOR BALLOON EXPANDABLE VALVES

CROSS-REFERENCE TO RELATED APPLICATIONS

This application claims priority to the filing date of U.S. Provisional Application No. 63/370,380, filed Aug. 4, 2022, the disclosure of which is hereby incorporated by reference herein.

BACKGROUND OF THE DISCLOSURE

Valvular heart disease, and specifically aortic and mitral valve disease, is a significant health issue in the United States. Valve replacement is one option for treating heart valve diseases. Prosthetic heart valves, including surgical heart valves and collapsible/expandable heart valves intended for transcatheter aortic valve replacement ("TAVR") or transcatheter mitral valve replacement ("TMVR"), are well known in the patent literature. Surgical or mechanical heart valves may be sutured into a native annulus of a patient during an open-heart surgical procedure, for example. Collapsible/expandable heart valves may be delivered into a patient via a tube-like delivery apparatus such as a catheter, a trocar, a laparoscopic instrument, or the like to avoid a more invasive procedure such as full open-chest, open-heart surgery. As used herein, reference to a "collapsible/expandable" heart valve includes heart valves that are formed with a small cross-section that enables them to be delivered into a patient through a tube-like delivery apparatus in a minimally invasive procedure, and then expanded to an operable state once in place, as well as heart valves that, after construction, are first collapsed to a small cross-section for delivery into a patient and then expanded to an operable size once in place in the valve annulus.

Collapsible/expandable prosthetic heart valves typically take the form of a one-way valve structure (often referred to as a valve assembly) mounted to/within an expandable stent. In general, these collapsible/expandable heart valves include a self-expanding or balloon-expandable stent, often made of nitinol or another shape-memory metal or a metal alloy (for self-expanding stents) or steel or cobalt-chromium (for balloon-expandable stents). Existing collapsible/expandable TAVR devices have been known to use different configurations of stent layouts—including straight vertical struts connected by "V"s as illustrated in U.S. Pat. No. 8,454,685, or diamond-shaped cell layouts as illustrated in U.S. Pat. No. 9,326,856, both of which are hereby incorporated herein by reference. The one-way valve assembly mounted to/within the stent includes one or more leaflets, and may also include a cuff or skirt. The cuff may be disposed on the stent's interior or luminal surface, its exterior or abluminal surface, and/or on both surfaces. A cuff helps to ensure that blood does not just flow around the valve leaflets if the valve or valve assembly is not optimally seated in a native valve annulus. A cuff, or a portion of a cuff disposed on the exterior of the stent, can help reduce or eliminate leakage around the outside of the valve (the latter known as paravalvular or "PV" leakage).

Balloon expandable valves are typically delivered to the native annulus while collapsed (or "crimped") onto a deflated balloon of a balloon catheter, with the collapsed valve being either partially or fully covered by an overlying sheath, or otherwise uncovered. Once the crimped prosthetic heart valve is positioned within the annulus of the native heart valve that is being replaced, the balloon is inflated to force the balloon-expandable valve to transition from the collapsed or crimped condition into an expanded or deployed condition, with the prosthetic heart valve tending to remain in the shape into which it is expanded by the balloon. Typically, when the position of the collapsed prosthetic heart valve is determined to be in the desired position relative to the native annulus (e.g. via visualization under fluoroscopy), a fluid (typically a liquid although gas could be used as well) such as saline is pushed via a syringe (manually, automatically, or semi-automatically) through the balloon catheter to cause the balloon to begin to fill and expand, and thus cause the overlying prosthetic heart valve to expand into the native annulus.

This disclosure generally focuses on various features of cuffs and leaflets used with a balloon-expandable prosthetic heart valve, as well as methods of assembling such features.

BRIEF SUMMARY OF THE DISCLOSURE

According to one aspect of the disclosure, a method of manufacturing a prosthetic heart valve includes coupling a plurality of prosthetic leaflets to each other, and coupling the plurality of prosthetic leaflets to a cuff, to form a valve assembly. The valve assembly may be coupled to a stent to form the prosthetic heart valve. The valve assembly may be formed prior to the plurality of prosthetic leaflets being coupled to the stent and prior to the cuff being coupled to the stent. Upon forming the valve assembly, the valve assembly may be in a flat condition. The plurality of prosthetic leaflets may each include a free edge, a scalloped edge, and tabs between the free edge and the scalloped edge. Coupling the plurality of prosthetic leaflets to the cuff may include coupling a portion of the free edge of each of the plurality of prosthetic leaflets to an edge of the cuff at spaced apart locations along the edge of the cuff. Forming the prosthetic heart valve may include positioning the plurality of prosthetic leaflets inside the stent, and wrapping the cuff around an inflow edge of the stent so that the cuff is positioned outside the stent. Coupling the valve assembly to the stent may include coupling the cuff to a luminal surface of the stent so that an extended portion of the cuff extends beyond an inflow edge of the stent and wrapping the extended portion of the cuff around the inflow edge of the stent so that the extended portion of the cuff is positioned on a luminal surface of the stent. Forming the valve assembly may include coupling a terminal edge of the extended portion of the cuff to the stent at spaced apart locations along the terminal edge of the extended portion of the cuff after wrapping the extended portion of the cuff around the inflow edge of the stent.

According to another aspect of the disclosure, a method of manufacturing a prosthetic heart valve may include forming a plurality of openings in a cuff. A plurality of cantilevered commissure attachment features of a stent may be passed through corresponding ones of the plurality of openings in the cuff. The cuff may be folded so that a first portion of the cuff is positioned on a luminal surface of the stent and a second portion of the cuff is positioned on an abluminal surface of the stent, the plurality of openings being positioned where the first portion of the cuff meets the second portion of the cuff. A plurality of prosthetic leaflets may be coupled to the first portion of the cuff. The plurality of prosthetic leaflets may be coupled to the first portion of the cuff prior to passing the plurality of cantilevered commissure attachment features of the stent through corresponding ones of the plurality of openings in the cuff.

A method of manufacturing a prosthetic heart valve may include coupling a cuff to a luminal surface of a stent so that an extended portion of the cuff extends beyond an inflow edge of the stent. The extended portion of the cuff may be wrapped around the inflow edge of the stent so that the extended portion of the cuff is positioned on an abluminal surface of the stent. A plurality of prosthetic leaflets may be coupled to the cuff using a plurality of stitches. Selected ones of the plurality of stitches may extend through the prosthetic leaflets, through a portion of the cuff on the luminal surface of the stent, and through a terminal edge of the extended portion of the cuff. No attachment mechanisms, besides the selected ones of the plurality of stitches, may couple the terminal edge of the extended portion of the cuff to the stent.

According to a further aspect of the disclosure, a method of manufacturing a prosthetic heart valve may include positioning a cuff on a luminal surface of a stent so that a first extended portion of the cuff extends beyond an inflow edge of the stent, and a second extended portion of the cuff extends beyond an outflow edge of the stent. The first extended portion of the cuff may be wrapped around the inflow edge of the stent so that the first extended portion of the cuff is positioned on an abluminal surface of the stent. The second extended portion of the cuff may be wrapped around the outflow edge of the stent so that the second extended portion of the cuff is positioned on the abluminal surface of the stent. The first extended portion of the cuff may be secured to the stent while the first extended portion of the cuff is positioned on the abluminal surface of the stent. The second extended portion of the cuff may be secured to the stent while the second extended portion of the cuff is positioned on the abluminal surface of the stent. A plurality of prosthetic leaflets may be mounted within the stent. Securing the second extended portion of the cuff to the stent may be performed using tack stitches. Securing the first extended portion of the cuff to the stent may include stitching a terminal edge of the first extended portion of the cuff to the stent at spaced locations in a circumferential direction of the stent so that openings are formed between circumferentially adjacent ones of the spaced locations, the openings providing a passageway for retrograde blood to flow into space between the first extended portion of the cuff and the portion of the cuff positioned on the luminal surface of the stent.

According to still another aspect of the disclosure, a method of manufacturing a prosthetic heart valve may include coupling an interior cuff to a luminal surface of a stent, the interior cuff having a plurality of interior cuff portions, each interior cuff portion having a straight outflow edge and a scalloped inflow edge, each interior cuff portion being coupled to an adjacent interior cuff portion by a connector. An exterior cuff may be coupled to an abluminal surface of the stent, the exterior cuff having a plurality of peaks and a plurality of troughs, each trough positioned between a pair of circumferentially adjacent peaks. A plurality of prosthetic leaflets may be coupled to corresponding ones of the interior cuff portions of the interior cuff. Each of the plurality of peaks of the exterior cuff may be aligned with space between an adjacent pair of interior cuff portions. The exterior cuff may include a paravalvular leak mitigation feature formed by a strip of cuff material positioned radially outward of the exterior cuff, a space between the paravalvular leak mitigation feature and the exterior cuff configured to receive retrograde blood flow therein. After coupling the interior cuff to the luminal surface of the stent, the exterior cuff to the abluminal surface of the stent, and the plurality of prosthetic leaflets to corresponding ones of the interior cuff portions, an opening may be formed between each interior cuff portion and a corresponding one of the plurality of troughs, the openings leading to exterior surfaces of the plurality of prosthetic leaflets so that retrograde blood flow passing through the openings pushes the plurality of prosthetic leaflets toward a closed position.

According to yet another aspect of the disclosure, A method of manufacturing a prosthetic heart valve may include positioning a cuff on a luminal surface of a stent so that an extended portion of the cuff extends beyond an inflow edge of the stent, and a plurality of tabs of the cuff extends beyond angled struts of the stent. The extended portion of the cuff may be wrapped around the inflow edge of the stent so that the first extended portion of the cuff is positioned on an abluminal surface of the stent. The plurality of tabs of the cuff may be wrapped around the angled struts of the stent, the plurality of tabs having pre-formed cuts separating adjacent ones of the plurality of tabs. The extended portion of the cuff may be secured to the portion of the cuff on the luminal surface of the stent while the extended portion of the cuff is positioned on the abluminal surface of the stent. The plurality of tabs may be secured to the portion of the cuff on the luminal surface of the stent while the plurality of tabs is positioned on the abluminal surface of the stent. A plurality of prosthetic leaflets may be mounted within the stent. The plurality of tabs may be secured to the portion of the cuff on the luminal surface of the stent using running stitches. The extended portion of the cuff may be secured to the portion of the cuff on the luminal surface of the stent using a circumferentially extending line of running stitches.

According to still a further aspect of the disclosure, a method of manufacturing a prosthetic heart valve includes positioning a cuff adjacent to a stent, the cuff including a plurality of outflow peaks, the stent including a plurality of cantilevered commissure attachment features. Each of the plurality of cantilevered commissure attachment features may be passed through a slit formed in a corresponding one of the plurality of outflow peaks of the cuff so that the outflow peaks are positioned on one of a luminal or abluminal surface of the stent, while a main body of the cuff is positioned on the other of the luminal or abluminal surface of the stent. The cuff may be secured to the stent. A plurality of prosthetic leaflets may be mounted inside the stent. Securing the cuff to the stent may include tying the cuff to the stent.

DETAILED DESCRIPTION

As used herein, the term "inflow end" when used in connection with a prosthetic heart valve refers to the end of the prosthetic valve into which blood first enters when the prosthetic valve is implanted in an intended position and orientation, while the term "outflow end" refers to the end of the prosthetic valve where blood exits when the prosthetic valve is implanted in the intended position and orientation. Thus, for a prosthetic aortic valve, the inflow end is the end nearer the left ventricle while the outflow end is the end nearer the aorta. The intended position and orientation are used for the convenience of describing the valve disclosed herein, however, it should be noted that the use of the valve is not limited to the intended position and orientation, but may be deployed in any type of lumen or passageway. For example, although the prosthetic heart valve is described herein as a prosthetic aortic valve, the same or similar structures and features can be employed in other heart valves, such as the pulmonary valve, the mitral valve, or the tricuspid valve. Further, the term "proximal," when used in connection with a delivery device or system, refers to a direction relatively close to the user of that device or system when being used as intended, while the term "distal" refers to a direction relatively far from the user of the device. In other words, the leading end of a delivery device or system is positioned distal to the trailing end of the delivery device or system, when being used as intended. As used herein, the terms "substantially," "generally," "approximately," and "about" are intended to mean that slight deviations from absolute are included within the scope of the term so modified. As used herein, the stent may assume an "expanded state" and a "collapsed state," which refer to the relative radial size of the stent.

Figure 1A:
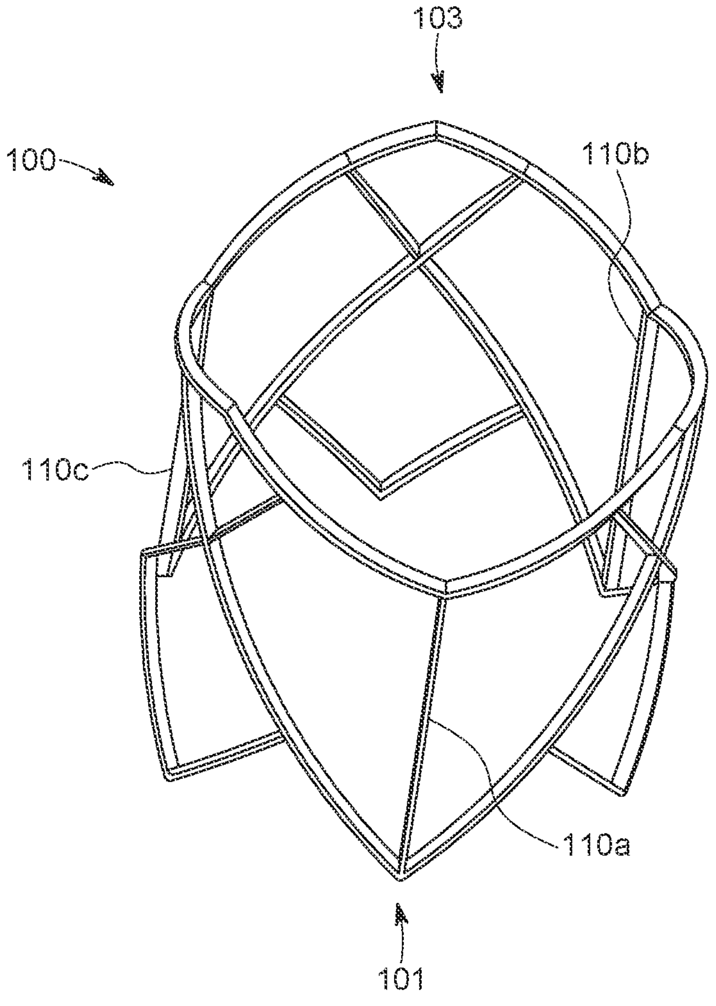
FIG. 1A is a perspective view of a stent of a prosthetic heart valve according to an embodiment of the disclosure.

FIG. 1A illustrates a perspective view of a stent 100 of a prosthetic heart valve according to an embodiment of the disclosure. Stent 100 may include a frame extending in an axial direction between an inflow end 101 and an outflow end 103. Stent 100 includes three generally symmetric sections, wherein each section spans about 120 degrees around the circumference of stent 100. Stent 100 includes three vertical struts 110*a*, 110*b*, 110*c*, that extend in an axial direction substantially parallel to the direction of blood flow through the stent, which may also be referred to as a central longitudinal axis. Each vertical strut 110*a*, 110*b*, 110*c* may extend substantially the entire axial length between the inflow end 101 and the outflow end 103 of the stent 100, and may be disposed between and shared by two sections. In other words, each section is defined by the portion of stent 100 between two vertical struts. Thus, each vertical strut 110*a*, 110*b*, 110*c* is also separated by about 120 degrees around the circumference of stent 100. It should be understood that, if stent 100 is used in a prosthetic heart valve having three leaflets, the stent may include three sections as illustrated. However, in other embodiments, if the prosthetic heart valve has two leaflets, the stent may only include two of the sections.

Figure 1B:
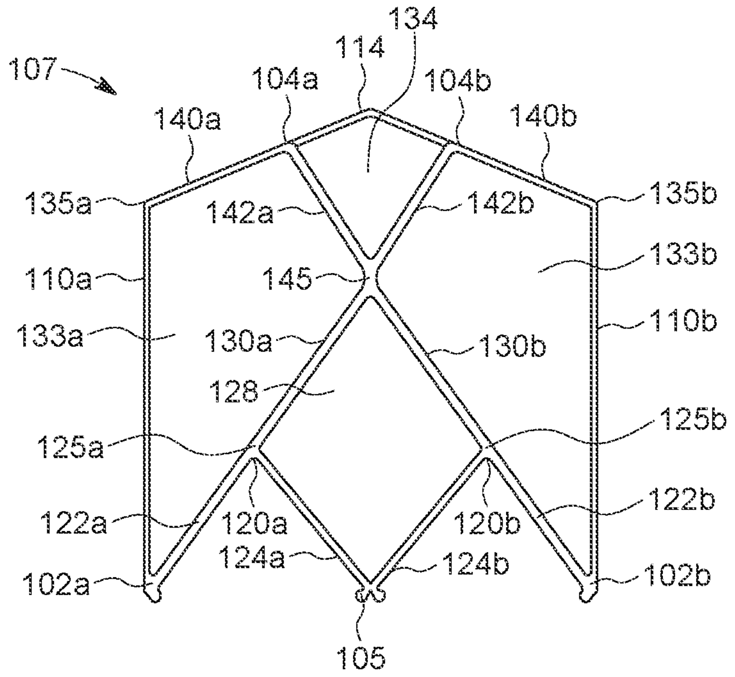
FIG. 1B is a schematic front view of a section of the stent of FIG. 1A.

FIG. 1B illustrates a schematic view of a stent section 107 of stent 100, which will be described herein in greater detail and which is representative of all three sections. Stent section 107 depicted in FIG. 1B includes a first vertical strut 110*a* and a second vertical strut 110*b*. First vertical strut 110*a* extends axially between a first inflow node 102*a* and a first outer node 135*a*. Second vertical strut 110*b* extends axially between a second inflow node 102*b* and a second outer node 135*b*. As is illustrated, the vertical struts 110*a*, 110*b* may extend almost the entire axial length of stent 100. In some embodiments, stent 100 may be formed as an integral unit, for example by laser cutting the stent from a tube. The term "node" may refer to where two or more struts of the stent 100 meet one another. A pair of sequential inverted V's extends between inflow nodes 102*a*, 102*b*, which includes a first inflow inverted V 120*a* and a second inflow inverted V 120*b* coupled to each other at an inflow node 105. First inflow inverted V 120*a* comprises a first outer lower strut 122*a* extending between first inflow node 102*a* and a first central node 125*a*. First inflow inverted V 120*a* further comprises a first inner lower strut 124*a* extending between first central node 125*a* and inflow node 105. A second inflow inverted V 120*b* comprises a second inner lower strut 124*b* extending between inflow node 105 and a second central node 125*b*. Second inflow inverted V 120*b* further comprises a second outer lower strut 122*b* extending between second central node 125*b* and second inflow node 102*b*. Although described as inverted V's, these structures may also be described as half-cells, each half cell being a half-diamond cell with the open portion of the half-cell at the inflow end 101 of the stent 100.

Stent section 107 further includes a first central strut 130*a* extending between first central node 125*a* and an upper node 145. Stent section 107 also includes a second central strut 130*b* extending between second central node 125*b* and upper node 145. First central strut 130*a*, second central strut 130*b*, first inner lower strut 124*a* and second inner lower strut 124*b* form a diamond cell 128. Stent section 107 includes a first outer upper strut 140*a* extending between first outer node 135 and a first outflow node 104*a*. Stent section 107 further includes a second outer upper strut 140*b* extending between second outer node 135*b* and a second outflow node 104*b*. Stent section 107 includes a first inner upper strut 142*a* extending between first outflow node 104*a* and upper node 145. Stent section 107 further includes a second inner upper strut 142*b* extending between upper node 145 and second outflow node 104*b*. Stent section 107 includes an outflow inverted V 114 which extends between first and second outflow nodes 104*a*, 104*b*. First vertical strut 110*a*, first outer upper strut 140*a*, first inner upper strut 142*a*, first central strut 130*a* and first outer lower strut 122*a* form a first generally kite-shaped cell 133*a*. Second vertical strut 110*b*, second outer upper strut 140*b*, second inner upper strut 142*b*, second central strut 130*b* and second outer lower strut 122*b* form a second generally kite-shaped cell 133*b*. First and second kite-shaped cells 133*a*, 133*b* are symmetric and opposite each other on stent section 107. Although the term "kite-shaped," is used above, it should be understood that such a shape is not limited to the exact geometric definition of kite-shaped. Outflow inverted V 114, first inner upper strut 142*a* and second inner upper strut 142*b* form upper cell 134. Upper cell 134 is generally kite-shaped and axially aligned with diamond cell 128 on stent section 107. It should be understood that, although designated as separate struts, the various struts described herein may be part of a single unitary structure as noted above. However, in other embodiments, stent 100 need not be formed as an integral structure and thus the struts may be different structures (or parts of different structures) that are coupled together.

Figure 1C:
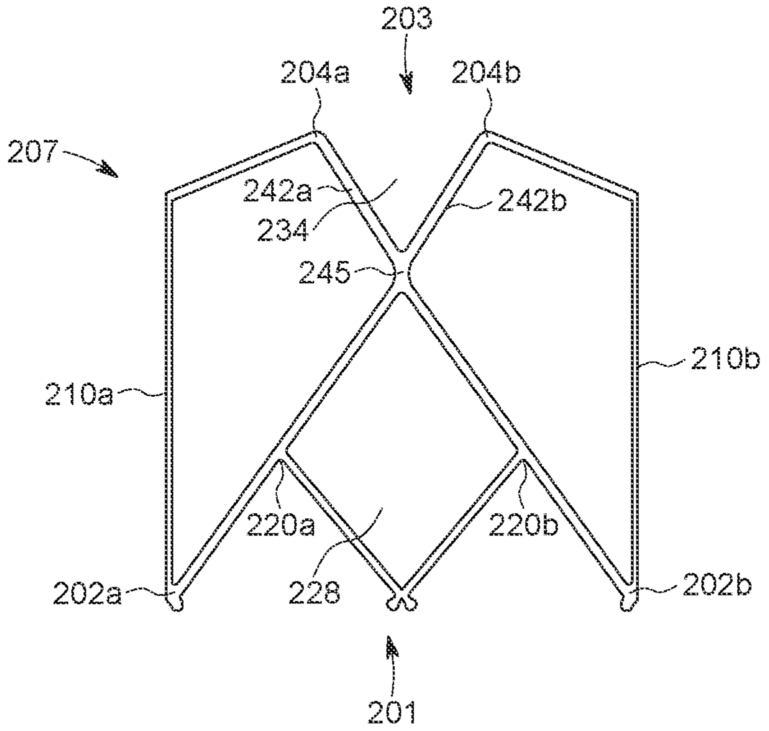
FIG. 1C is a schematic front view of a section of a stent according to an alternate embodiment of the prosthetic heart valve of FIG. 1A.

FIG. 1C illustrates a schematic view of a stent section 207 according to an alternate embodiment of the disclosure. Unless otherwise stated, like reference numerals refer to like elements of above-described stent 100 but within the 200-series of numbers. Stent section 207 is substantially similar to stent section 107, including inflow nodes 202*a*, 202*b*, vertical struts 210*a*, 210*b*, first and second inflow inverted V's 220*a*, 220*b* and outflow nodes 204*a*, 204*b*. The structure of stent section 207 departs from that of stent section 107 in that it does not include an outflow inverted V. The purpose of an embodiment having such structure of stent section 207 shown in FIG. 1C is to reduce the required force to expand the outflow end 203 of the stent 200, compared to stent 100, to promote uniform expansion relative to the inflow end 201. Outflow nodes 204*a*, 204*b* are connected by a properly oriented V formed by first inner upper strut 242*a*, upper node 245 and second inner upper strut 242*b*. In other words, struts 242*a*, 242*b* may form a half diamond cell 234, with the open end of the half-cell oriented toward the outflow end 203. Half diamond cell 234 is axially aligned with diamond cell 228. Adding an outflow inverted V coupled between outflow nodes 204*a*, 204*b* contributes additional material that increases resistance to modifying the stent shape and requires additional force to expand the stent. The exclusion of material from outflow end 203 decreases resistance to expansion on outflow end 203, which may promote uniform expansion of inflow end 201 and outflow end 203. In other words, the inflow end 201 of stent 200 does not include continuous circumferential structure, but rather has mostly or entirely open half-cells with the open portion of the half-cells oriented toward the inflow end 201, whereas most of the outflow end 203 includes substantially continuous circumferential structure, via struts that correspond with struts 140*a*, 140*b*. All else being equal, a substantially continuous circumferential structure may require more force to expand compared to a similar but open structure. Thus, the inflow end 101 of stent 100 may require more force to radially expand compared to the outflow end 103. By omitting inverted V 114, resulting in stent 200, the force required to expand the outflow end 203 of stent 200 may be reduced to an amount closer to the inflow end 201.

Figure 1D:
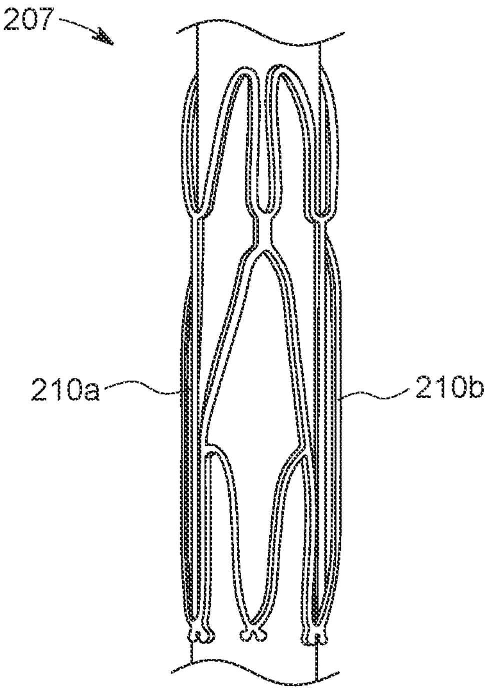
FIGS. 1D-E are front views of the stent section of FIG. 1C in a collapsed and expanded state, respectively.
Figure 1E:
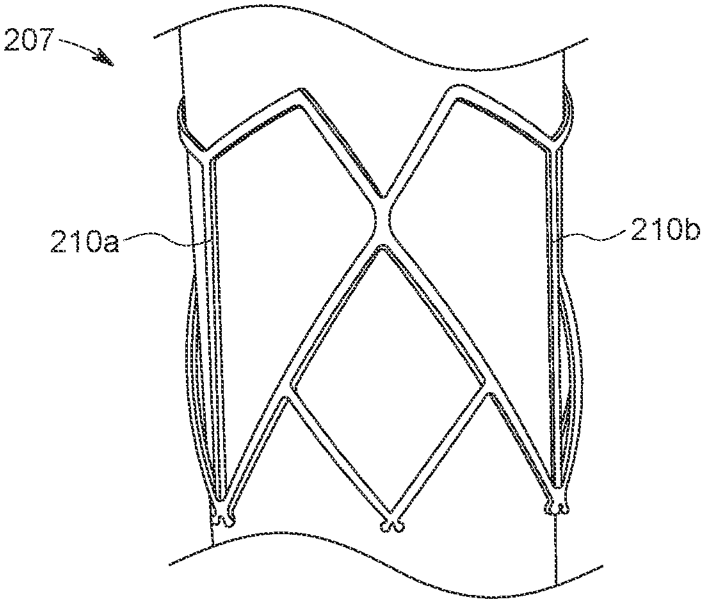
Figure 1F:
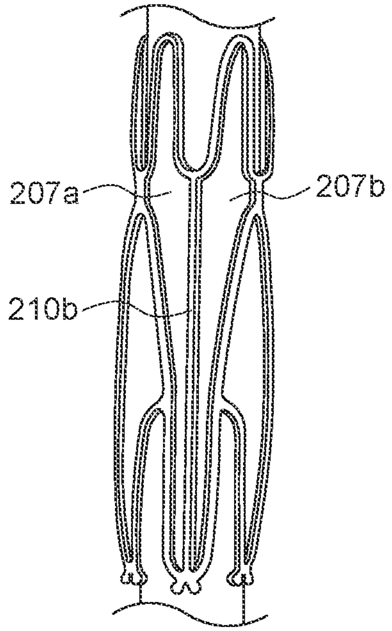
FIGS. 1F-G are side views of a portion of the stent according to the embodiment of FIG. 1C in a collapsed and expanded state, respectively.
Figure 1G:
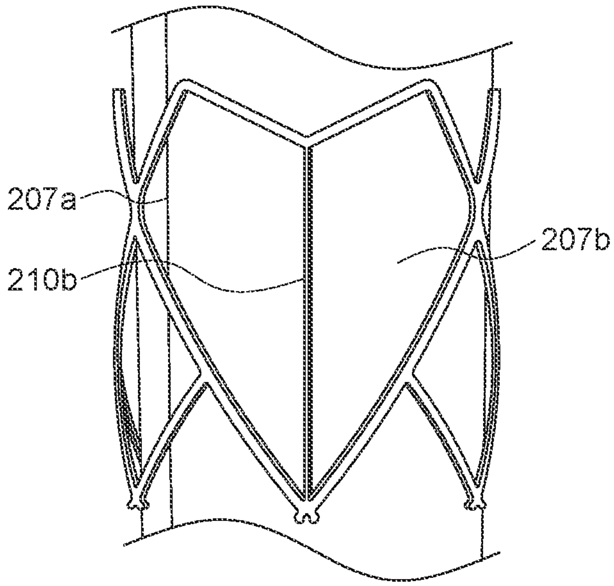

FIG. 1D shows a front view of stent section 207 in a collapsed state and FIG. 1E shows a front view of stent section 207 in an expanded state. It should be understood that stent 200 in FIGS. 1D-E is illustrated with an opaque tube extending through the interior of the stent, purely for the purpose of helping illustrate the stent, and which may represent a balloon over which the stent section 207 is crimped. As described above, a stent comprises three symmetric sections, each section spanning about 120 degrees around the circumference of the stent. Stent section 207 illustrated in FIGS. 1D-E is defined by the region between vertical struts 210*a*, 210*b*. Stent section 207 is representative of all three sections of the stent. Stent section 207 has an arcuate structure such that when three sections are connected, they form one complete cylindrical shape. FIGS. 1F-G illustrate a portion of the stent from a side view. In other words, the view of stent 200 in FIGS. 1F-G is rotated about 60 degrees compared to the view of FIGS. 1D-E. The view of the stent depicted in FIGS. 1F-G is centered on vertical strut 210*b* showing approximately half of each of two adjacent stent sections 207*a*, 207*b* on each side of vertical strut 210*b*. Sections 207*a*, 207*b* surrounding vertical strut 210*b* are mirror images of each other. FIG. 1F shows stent sections 207*a*, 207*b* in a collapsed state whereas FIG. 1G shows stent sections 207*a*, 207*b* in an expanded state.

Figure 1H:
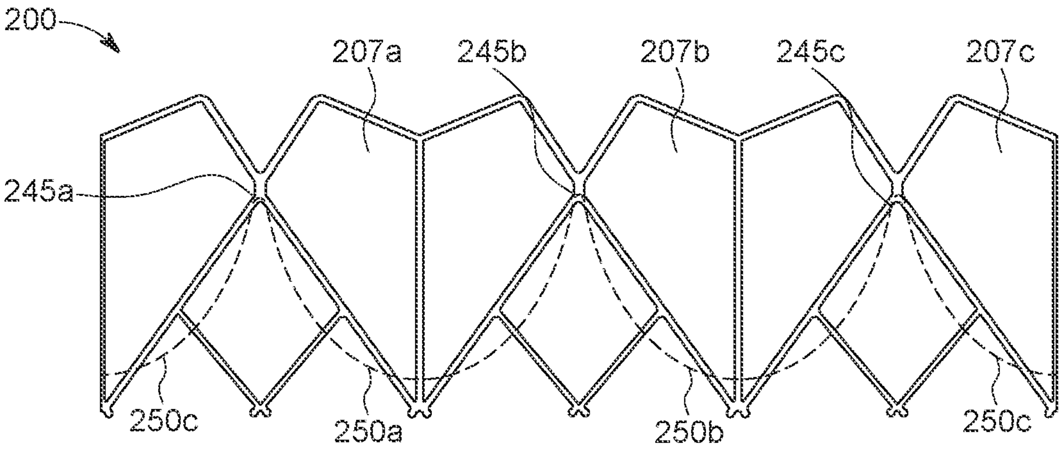
FIG. 1H is a flattened view of the stent according to the embodiment of FIG. 1C, as if cut and rolled flat.

FIG. 1H illustrates a flattened view of stent 200 including three stent sections 207*a*, 207*b*, 207*c*, as if the stent has been cut longitudinally and laid flat on a table. As depicted, sections 207*a*, 207*b*, 207*c* are symmetric to each other and adjacent sections share a common vertical strut. As described above, stent 200 is shown in a flattened view, but each section 207*a*, 207*b*, 207*c* has an arcuate shape spanning 120 degrees to form a full cylinder. Further depicted in FIG. 1H are leaflets 250*a*, 250*b*, 250*c* coupled to stent 200. However, it should be understood that only the connection of leaflets 250*a-c* is illustrated in FIG. 1H. In other words, each leaflet 250*a-c* would typically include a free edge, with the free edges acting to coapt with one another to prevent retrograde flow of blood through the stent 200, and the free edges moving radially outward toward the interior surface of the stent to allow antegrade flow of blood through the stent. Those free edges are not illustrated in FIG. 1H. Rather, the attached edges of the leaflets 250*a-c* are illustrated in dashed lines in FIG. 1H. Although the attachment may be via any suitable modality, the attached edges may be preferably sutured to the stent 200 and/or to an intervening cuff or skirt between the stent and the leaflets 250*a-c*. Each of the three leaflets 250*a*, 250*b*, 250*c*, extends about 120 degrees around stent 200 from end to end and each leaflet includes a belly that may extend toward the radial center of stent 200 when the leaflets are coapted together. Each leaflet extends between the upper nodes of adjacent sections. First leaflet 250*a* extends from first upper node 245*a* of first stent section 207*a* to second upper node 245*b* of second stent section 207*b*. Second leaflet 250*b* extends from second upper node 245*b* to third upper node 245*c* of third stent section 207*c*. Third leaflet 250*c* extends from third upper node 245*c* to first upper node 245*a*. As such, each upper node includes a first end of a first leaflet and a second end of a second leaflet coupled thereto. In the illustrated embodiment, each end of each leaflet is coupled to its respective node by suture. However, any coupling means may be used to attach the leaflets to the stent. It is further contemplated that the stent may include any number of sections and/or leaflets. For example, the stent may include two sections, wherein each section extends 180 degrees around the circumference of the stent. Further, the stent may include two leaflets to mimic a bicuspid valve. Further, it should be noted that each leaflet may include tabs or other structures (not illustrated) at the junction between the free edges and attached edges of the leaflets, and each tab of each leaflet may be coupled to a tab of an adjacent leaflet to form commissures. In the illustrated embodiment, the leaflet commissures are illustrated attached to nodes where struts intersect. However, in other embodiments, the stent 200 may include commissure attachment features built into the stent to facilitate such attachment. For example, commissures attachment features may be formed into the stent 200 at nodes 245*a-c*, with the commissure attachment features including one or more apertures to facilitate suturing the leaflet commissures to the stent. Further, leaflets 250*a-c* may be formed of a biological material, such as animal pericardium, or may otherwise be formed of synthetic materials, such as ultra-high molecular weight polyethylene (UHMWPE).

Figure 1I:
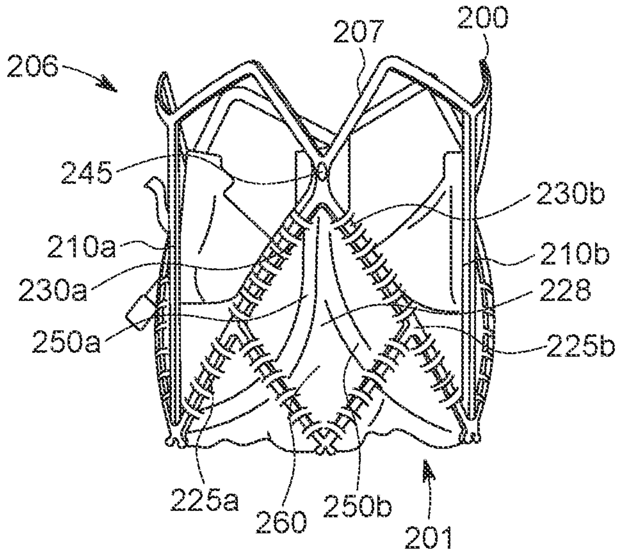
FIGS. 1I-J are front and side views, respectively, of a prosthetic heart valve including the stent of FIG. 1C.
Figure 1J:
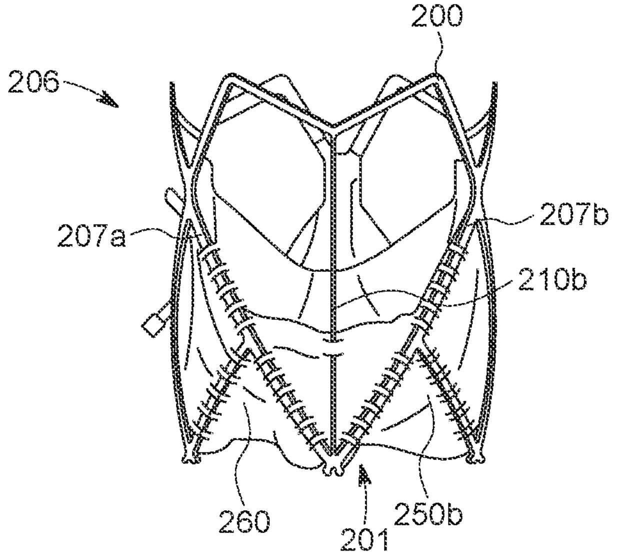

FIGS. 1I-J illustrate prosthetic heart valve 206, which includes stent 200, a cuff 260 coupled to stent 200 (for example via sutures) and leaflets 250*a*, 250*b*, 250*c* attached to stent 200 and/or cuff 260 (for example via sutures). Prosthetic heart valve 206 is intended for use in replacing an aortic valve, although the same or similar structures may be used in a prosthetic valve for replacing other heart valves. Cuff 260 is disposed on a luminal or interior surface of stent 200, although the cuff could be disposed alternately or additionally on an abluminal or exterior surface of the stent. The cuff 260 may include an inflow end disposed substantially along inflow end 201 of stent 200. FIG. 1I shows a front view of valve 206 showing one stent portion 207 between vertical struts 210*a*, 210*b* including cuff 260 and an outline of two leaflets 250*a*, 250*b* sutured to cuff 260. Different methods of suturing leaflets to the cuff as well as the leaflets and/or cuff to the stent may be used, many of which are described in U.S. Pat. No. 9,326,856 which is hereby incorporated by reference. In the illustrated embodiment, the upper (or outflow) edge of cuff 260 is sutured to first central node 225*a*, upper node 245 and second central node 225*b*, extending along first central strut 230*a* and second central strut 230*b*. The upper (or outflow) edge of cuff 260 continues extending approximately between the second central node of one section and the first central node of an adjacent section. Cuff 260 extends between upper node 245 and inflow end 201. Thus, cuff 260 covers the cells of stent portion 207 formed by the struts between upper node 245 and inflow end 201, including diamond cell 228. FIG. 1J illustrates a side view of stent 200 including cuff 260 and an outline of leaflet 250*b*. In other words, the view of valve 206 in FIG. 1J is rotated about 60 degrees compared to the view of FIG. 1I. The view depicted in FIG. 1J is centered on vertical strut 210*b* showing approximately half of each of two adjacent stent sections 207*a*, 207*b* on each side of vertical strut 210*b*. Sections 207*a*, 207*b* surrounding vertical strut 210*b* are mirror images of each other. As described above, the cuff may be disposed on the stent's interior or luminal surface, its exterior or abluminal surface, and/or on both surfaces. A cuff ensures that blood does not just flow around the valve leaflets if the valve or valve assembly are not optimally seated in a valve annulus. A cuff, or a portion of a cuff disposed on the exterior of the stent, can help retard leakage around the outside of the valve (the latter known as paravalvular leakage or "PV" leakage). In the embodiment illustrated in FIGS. 1I-J, the cuff 260 only covers about half of the stent 200, leaving about half of the stent uncovered by the cuff. With this configuration, less cuff material is required compared to a cuff that covers more or all of the stent 200. Less cuff material may allow for the prosthetic heart valve 206 to crimp down to a smaller profile when collapsed. It is contemplated that the cuff may cover any amount of surface area of the cylinder formed by the stent. For example, the upper edge of the cuff may extend straight around the circumference of any cross section of the cylinder formed by the stent. Cuff 260 may be formed of any suitable material, including a biological material such as animal pericardium, or a synthetic material such as UHMWPE.

Figure 1K:
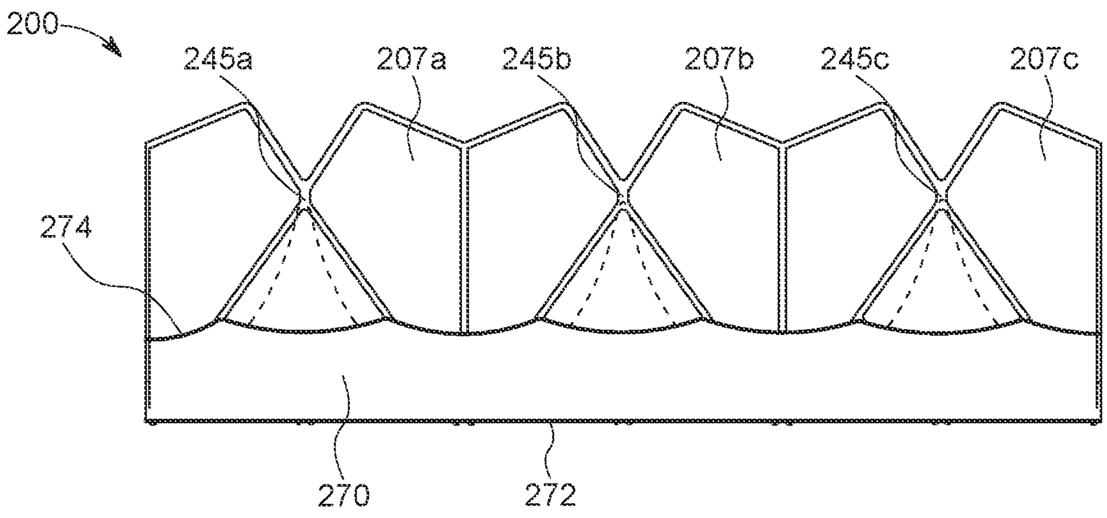
FIG. 1K illustrates the view of FIG. 1H with an additional outer cuff provided on the stent.

As noted above, FIGS. 1I-J illustrate a cuff 260 positioned on an interior of the stent 200. An example of an additional outer cuff 270 is illustrated in FIG. 1K. It should be understood that outer cuff 270 may take other shapes than that shown in FIG. 1K. The outer cuff 270 shown in FIG. 1K may be included without an inner cuff 260, but preferably is provided in addition to an inner cuff 260. The outer cuff 270 may be formed integrally with the inner cuff 260 and folded over (e.g. wrapped around) the inflow edge of the stent, or may be provided as a member that is separate from inner cuff 260. Outer cuff 270 may be formed of any of the materials described herein in connection with inner cuff 260. In the illustrated embodiment, outer cuff 270 includes an inflow edge 272 and an outflow edge 274. If the inner cuff 260 and outer cuff 270 are formed separately, the inflow edge 272 may be coupled to an inflow end of the stent 200 and/or an inflow edge of the inner cuff 260, for example via suturing, ultrasonic welding, or any other suitable attachment modality. The coupling between the inflow edge 272 of the outer cuff 270 and the stent 200 and/or inner cuff 260 preferably results in a seal between the inner cuff 260 and outer cuff 270 at the inflow end of the prosthetic heart valve so that any retrograde blood that flows into the space between the inner cuff 260 and outer cuff 270 is unable to pass beyond the inflow edges of the inner cuff 260 and outer cuff 270. The outflow edge 274 may be coupled at selected locations around the circumference of the stent 200 to struts of the stent 200 and/or to the inner cuff 260, for example via sutures. With this configuration, an opening may be formed between the inner cuff 260 and outer cuff 270 circumferentially between adjacent connection points, so that retrograde blood flow will tend to flow into the space between the inner cuff 260 and outer cuff 270 via the openings, without being able to continue passing beyond the inflow edges of the cuffs. As blood flows into the space between the inner cuff 260 and outer cuff 270, the outer cuff 270 may billow outwardly, creating even better sealing between the outer cuff 270 and the native valve annulus against which the outer cuff 270 presses. The outer cuff 270 may be provided as a continuous cylindrical member, or a strip that is wrapped around the outer circumference of the stent 200, with side edges, which may be parallel or non-parallel to a center longitudinal axis of the prosthetic heart valve, attached to each other so that the outer cuff 270 wraps around the entire circumference of the stent 200.

The stent may be formed from biocompatible materials, including metals and metal alloys such as cobalt chrome (or cobalt chromium) or stainless steel, although in some embodiments the stent may be formed of a shape memory material such as nitinol or the like. The stent is thus configured to collapse upon being crimped to a smaller diameter and/or expand upon being forced open, for example via a balloon within the stent expanding, and the stent will substantially maintain the shape to which it is modified when at rest. The stent may be crimped to collapse in a radial direction and lengthen (to some degree) in the axial direction, reducing its profile at any given cross-section. The stent may also be expanded in the radial direction and foreshortened (to some degree) in the axial direction.

The prosthetic heart valve may be delivered via any suitable transvascular route, for example including transapically or transfemorally. Generally, transapical delivery utilizes a relatively stiff catheter that pierces the apex of the left ventricle through the chest of the patient, inflicting a relatively higher degree of trauma compared to transfemoral delivery. In a transfemoral delivery, a delivery device housing the valve is inserted through the femoral artery and threaded against the flow of blood to the left ventricle. In either method of delivery, the valve may first be collapsed over an expandable balloon while the expandable balloon is deflated. The balloon may be coupled to or disposed within a delivery system, which may transport the valve through the body and heart to reach the aortic valve, with the valve being disposed over the balloon (and, in some circumstances, under an overlying sheath). Upon arrival at or adjacent the aortic valve, a surgeon or operator of the delivery system may align the prosthetic valve as desired within the native valve annulus while the prosthetic valve is collapsed over the balloon. When the desired alignment is achieved, the overlying sheath, if included, may be withdrawn (or advanced) to uncover the prosthetic valve, and the balloon may then be expanded causing the prosthetic valve to expand in the radial direction, with at least a portion of the prosthetic valve foreshortening in the axial direction.

Figure 2A:
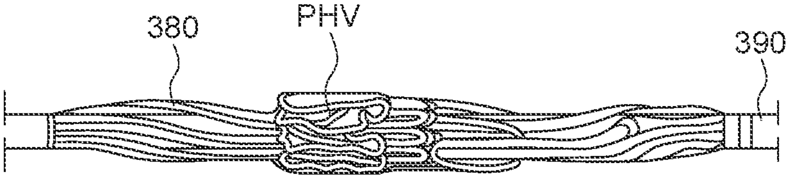
FIG. 2A illustrates a prosthetic heart valve crimped over a balloon of a delivery device in a delivery condition.
Figure 2B:
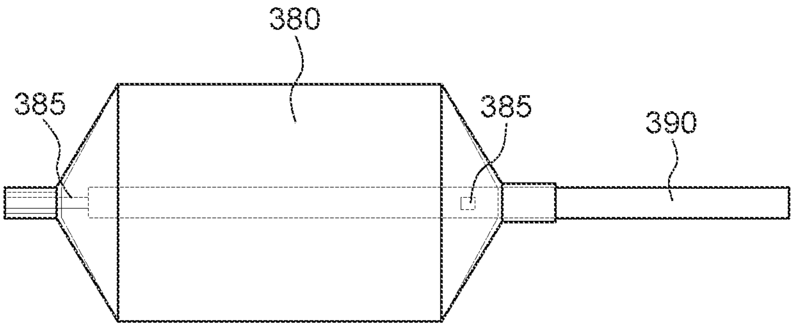
FIG. 2B illustrates the balloon of FIG. 2A after being inflated.

Referring to FIG. 2A, an example of a prosthetic heart valve PHV, which may include a stent similar to stents 100 or 200, is shown crimped over a balloon 380 of a balloon catheter 390 while the balloon 380 is in a deflated condition. It should be understood that other components of the delivery device, such as a handle used for steering and/or deployment, as well as a syringe for inflating the balloon 380, are omitted from FIGS. 2A-B. The prosthetic heart valve PHV may be delivered intravascularly, for example through the femoral artery, around the aortic arch, and into the native aortic valve annulus, while in the crimped condition shown in FIG. 2A. Once the desired position is obtained, fluid may be pushed through the balloon catheter 390 to inflate the balloon 380, as shown in FIG. 2B. FIG. 2B omits the prosthetic heart valve PHV, but it should be understood that, as the balloon 380 inflates, it forces the prosthetic heart valve PHV to expand into the native aortic valve annulus (although it should be understood that other heart valves may be replaced using the concepts described herein). In the illustrated example, fluid flows from a syringe (not shown) into the balloon 380 through a lumen within balloon catheter 390 and into one or more ports 385 located internal to the balloon 380. In the particular illustrated example of FIG. 2B, a first port 385 may be one or more apertures in a side wall of the balloon catheter 390, and a second port 385 may be the distal open end of the balloon catheter 390, which may terminate within the interior space of the balloon 380.

Figure 3:
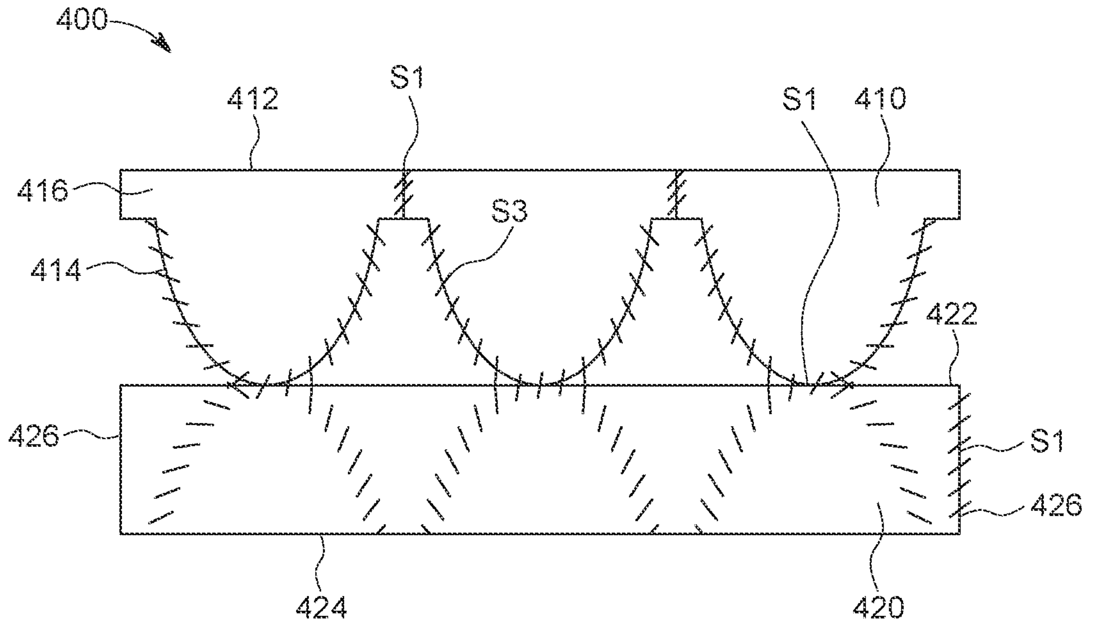
FIG. 3 is a highly schematic view of a valve assembly in an early stage of manufacture.
Figure 4:
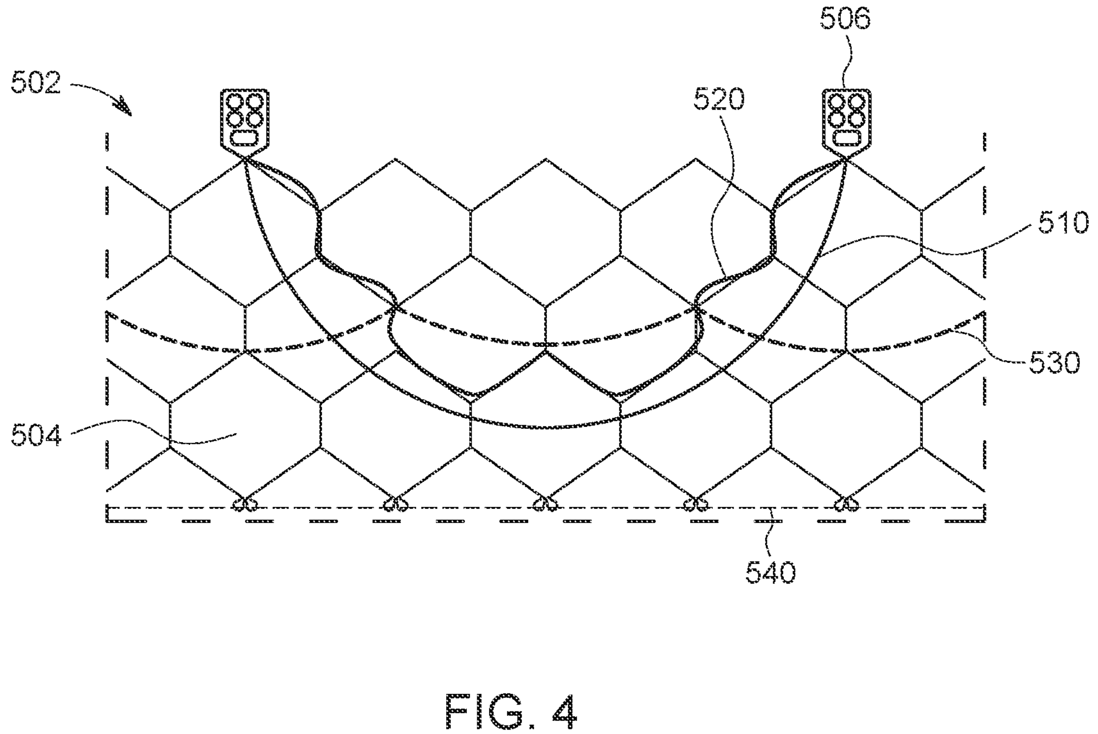
FIG. 4 is a highly schematic view of a valve assembly coupled to a stent.

FIGS. 3 and 4 are generally directed to prosthetic leaflets that are pre-assembled to a cuff prior to coupling the leaflets and cuff to the stent of a prosthetic heart valve.

Referring to FIG. 3, a valve assembly 400 in a stage of assembly is shown. A plurality of prosthetic leaflets 410 may be provided. In this example, three leaflets 410 are provided, but more or fewer may be provided in other embodiments. The leaflets 410 may be formed of any suitable material, including tissue (e.g., porcine or bovine pericardium) or synthetic materials (e.g. polytetrafluroethylene ("PTFE"), polyethylene terephthalate ("PET") or ultra-high molecular weight polyethylene ("UHMWPE"). Each leaflet 410 may have a free edge 412, an attached edge 414, and a tab 416 on each side where the free edge 412 meets the attached edge 414. After assembly, the free edges 412 of the leaflets 410 may coapt with each other to block the retrograde flow of blood through the valve assembly 400 and move away from each other to allow the antegrade flow of blood through the valve assembly 400. After assembly, the attached edges 414 may be attached to a stent (e.g., any stent described herein or any other suitable frame) and/or a cuff to secure the leaflets 410 to the stent. The valve assembly 400 shown in FIG. 3 also includes a skirt or cuff 420, which may be formed of tissue or synthetic materials (e.g., woven PET or woven PTFE), similar to the leaflets 410. In this particular example, the cuff 420 is generally rectangular, with a generally straight inflow edge 422, a generally straight outflow edge 424, and two generally straight side edges 426. However, it should be understood that the specific shapes of both the leaflets 410 and the cuff of 420 of FIG. 3 may be modified and other shapes may be suitable. For example, the cuff 420 may be provided with oblique side edges and the outflow edge 424 may be provided with scallops.

Still referring to FIG. 3, in the first stage of assembling the valve assembly 400, the leaflets 410 may be pre-assembled to each other and to the cuff 420. For example, the tab 416 of one leaflet 410 may be coupled (e.g., via sutures S1) to the tab 416 of an adjacent leaflet 410. The inflow edge 422 of the cuff 420 may also be attached, for example via suturing, at selected locations to the attached edge 414 of each leaflet 410. For example, locations near the bottom-most (or proximal-most or inflow-most) contour of the attached edge 414 may be coupled (e.g., via sutures S1) to the inflow edge 422 of the cuff 420. During this pre-assembly, the side edges 426 of the cuff 420 may be coupled to each other (e.g., via sutures S1) and any remaining unconnected tabs 416 of the leaflets 410 may be connected to each other so that both the leaflets 410 and the cuff 420 are in a generally circular or cylindrical profile. It should be understood that the connections described for the pre-assembly may be completed in any order. For example, the side edges 426 of the cuff 420 could be connected to each other first to form a cylindrical cuff 420, and then the leaflets 410 may be coupled to the cuff 420. However, it may be preferable to attach the leaflets 410 to the cuff 420 as shown in FIG. 3, while generally flat on a table, prior to connecting the side edges 426 of the cuff to each other and prior to connecting the two remaining tabs 416 of the leaflets 410 to each other. In some embodiments, a separate inner cuff may be provided for each leaflet, where each leaflet is preassembled first to its respective inner cuff.

After this first stage of assembly, the second stage of assembly may be performed in which the leaflets 410 are positioned inside of the stent, and the cuff 420 is folded up over the exterior or abluminal surface of the stent, such that the stent is positioned between the leaflets 410 and the cuff 420. Preferably, in this second stage of assembly, the inflow edge of the stent is positioned at or adjacent to the location where the leaflets 410 are coupled (e.g., via sutures S1) to the cuff 420.

In the third stage of assembly occurring after the second stage described above, the valve assembly 400 may be lined up with the struts of the stent in the desired position, and the belly of the leaflet may be coupled (e.g., via sutures S3 along the attached edge 414) as needed to the cuff 420. In this embodiment, the inflow edge 422 of the cuff 420 does not need to have a continuous suture line to the inflow edge of the stent. It should be noted that sutures S3 are shown in FIG. 3 at their intended location after the cuff 420 is folded up over the inflow end of the stent. In other words, the sutures S3 shown in FIG. 3 would not exist when the valve assembly 400 is in the first stage of assembly. The sutures S3 may connect to the leaflets, inner/outer cuff(s), and any combination thereof.

Forming a prosthetic heart valve by using the method described above in connection with valve assembly 400 may provide a number of potential advantages. One potential advantage is that, by pre-assembling the leaflets 410 to each other and to the cuff 420, particularly while the components are "flat" on the table, the assembly process may be easier, faster, more accurate, and create more reproducible results compared to a more traditional assembly that occurs while the components are within or on the stent and not flat on a table. Another potential advantage is that good sealing may be obtained without the need for an inner cuff (e.g., a cuff positioned between the leaflets 410 and the stent). The elimination of an inner cuff may be useful because, compared to a similar prosthetic valve with an inner cuff, the prosthetic valve without an inner cuff will typically be able to collapse down to a smaller profile and be generally less "bulky" which may allow a smaller delivery catheter to be used, which is generally preferable.

FIG. 4 shows another option involving the pre-assembly of a cuff to leaflets. In particular, FIG. 4 shows a frame or stent 502, which may be a self-expanding or balloon-expandable frame, that generally includes three rows of substantially identical hexagonal or diamond-shaped cells 504, with commissure attachment features ("CAFs") 506 extending in a cantilevered fashion from selected cells 504 at the outflow end of the stent 502. However, it should be understood that the concepts described in connection with FIG. 4 may apply equally to stents having a different configuration than stent 502. For purposes of clarity, the actual leaflets and cuff of the valve assembly of FIG. 4 are not shown—rather lines representing where sutures couple portions of the valve assembly are shown. In particular, a leaflet attachment line 510 is illustrated as a generally parabolic line extending between an adjacent pair of CAFs 506. This attachment line 510 shows where the bottom edge of the leaflet (or the "attached edge," similar to attached edge 414 of FIG. 3) is sutured to the cuff. Although a single leaflet attachment line 510 is shown, the prosthetic valve would include one leaflet attachment line 510 per leaflet, for example for a total of three leaflet attachment lines 510 for a three-leaflet valve. As with the embodiment of FIG. 3, each leaflet used in the embodiment of FIG. 4 may include leaflet tabs that are attached to each other as part of the preassembly process, with the leaflets also attached to the cuff along leaflet attachment line(s) 510 prior to either the leaflets or the cuff being attached to the frame 502. The cuff may be sized and shaped so that, upon preassembly of the leaflets to the cuff, at least a portion of the cuff may extend above (in the outflow direction) the leaflet attachment line 510, with the cuff also extending a significant distance below the leaflets. With this configuration, the cuff will include excess material that may be folded over the inflow edge of the stent 502 to create an outer cuff, as described below.

After the leaflets are attached to the cuff along leaflet attachment line(s) 510, for example via sutures, the leaflet-cuff assembly may be coupled to the inner or luminal surface of the stent 502. For example, the leaflets may be coupled to the CAFs 506, for example via suturing at the leaflet tabs, and the cuff may be attached to the stent 502, for example via suturing, along inner cuff attachment line(s) 520. The inner cuff attachment line(s) 520 may consist of suture connections between only the cuff and struts of the stent 502 that form the cells 504. Preferably, the inner cuff attachment line(s) 520 generally follow the leaflet attachment line(s) 510, but because the inner cuff attachment line(s) 520 follow the linear struts of the cells 504, the inner cuff attachment line(s) 520 includes a plurality of generally straight lines that, in the aggregate, follow a generally parabolic shape. Preferably, all points of the inner cuff attachment line(s) 520 are positioned at or above (in the outflow direction) corresponding points of the leaflet attachment line(s) 510. As with the leaflet attachment line(s) 510, although only a single inner cuff attachment line 520 is shown between CAFs 506, there would typically be one inner cuff attachment line 520 between each pair of adjacent CAFs 506.

After the leaflets have been preassembled to the cuff along leaflet attachment line(s) 510, and after the leaflet-cuff assembly has been attached to the frame 502 along inner cuff attachment line(s) 520, a significant length of the cuff preferably extends beyond (in the inflow direction) the bottom of the stent 502. This excess cuff material may be folded around the inflow edge of the stent 502, for example at fold line 540, to create an outer cuff. The outer cuff may then be coupled, for example via sutures, to the stent 502 to secure the outer cuff. One example of the contours of the terminal edge of the outer cuff is shown at contour line 530. In some embodiments, the outer cuff may be coupled to the inner cuff and/or the stent 502 via a substantially continuous suture line following contour 530. However, in other embodiments, the terminal edge of the outer cuff is only coupled to the stent 502 and/or inner cuff, for example via sutures, at locations where the contour line 530 crosses a strut of the stent 502. With this attachment methodology, openings may be created between the attachment points so that retrograde blood flowing around the outside of the stent 502 may flow into the space between the inner and outer cuff portions, which may help trap blood and force the outer cuff into better engagement and/or sealing with the native valve annulus. In this embodiment in which a single cuff element wraps around the inflow edge of the stent 502 to form inner and outer cuff portions, the cuff is preferably not directly connected to the stent 502 (e.g., by sutures) at or near fold line 530. Avoiding direct connections at these locations may help allow the stent 502 to collapse and expand radially (and thus lengthen and foreshorten axially) without the cuff overly limiting the ability of the stent 502 to collapse and expand.

One potential advantage of the assembly of FIG. 4 is that, by pre-assembling the leaflets to each other and to the cuff, particularly while the components are "flat" on the table, the assembly process may be easier, faster, more accurate, and create more reproducible results compared to a more traditional assembly that occurs while the components are within or on the stent and not flat on a table. In addition, by using a single cuff that folds over the inflow edge of the stent 502, rather than using separate inner and outer cuffs, fewer sutures may be required to attach the cuff to the stent 502, which may result in a less bulky finished product and may require less time and complexity since fewer sutures are required.

A number of cuff assembly techniques are described below that may be beneficial for various reasons, whether or not the cuff is preassembled to the leaflets as described in connection with FIGS. 3-4.

Figure 5:
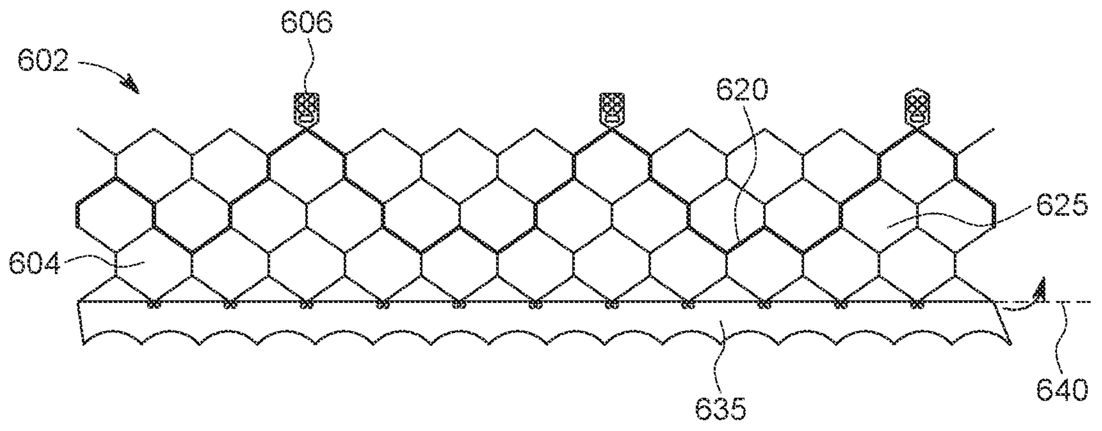
FIG. 5 illustrates a plan view of a stent with a cuff during a stage of assembly of the cuff to the stent.

FIG. 5 illustrates a stent 602 that is substantially identical to stent 502, although the concepts disclosed in connection with FIG. 5 may work equally well for other self- or balloon-expandable stent designs. Stent 602 may include a plurality of cells 604 formed by struts, the cells 604 being generally diamond-shaped or hexagonal. As with stent 502, stent 602 may include a plurality of CAFs 606, which in this example are also cantilevered and number three in total. The outline of a cuff is shown in a middle stage of assembly to the stent 602. The cuff, along with all other cuffs described herein, may be formed of tissue and/or synthetic materials, including those described in connection with any other cuffs described herein. Upon attachment to the inner surface of the stent 602, the cuff may form an inner cuff portion 625 that is attached to the stent 602 along inner cuff attachment line 620, which may be similar or identical to that described in connection with FIG. 4. After coupling the cuff to the luminal surface of the stent 602 along inner cuff attachment line 620, an extended portion 635 of the cuff may protrude below the bottom (or inflow edge) of the stent 602. The extended portion 635 may be folded or wrapped over the inflow edge of the stent 602 about fold line 640 to form an outer cuff (not shown). The terminal edge of the outer cuff may be coupled (e.g., via suturing) to the stent 602 in substantially the same manner described above in connection with FIG. 4. If the cuff of FIG. 5 is preassembled to leaflets prior to attachment to the stent 602, the embodiment of FIG. 5 may be similar or identical to that of FIG. 4. However, FIG. 5 illustrates that the cuff folding technique of FIG. 4 may be applicable to stent 602 even if the leaflets are only attached to the cuff and/or stent 602 after the cuff is attached to the stent 602.

Figure 6:
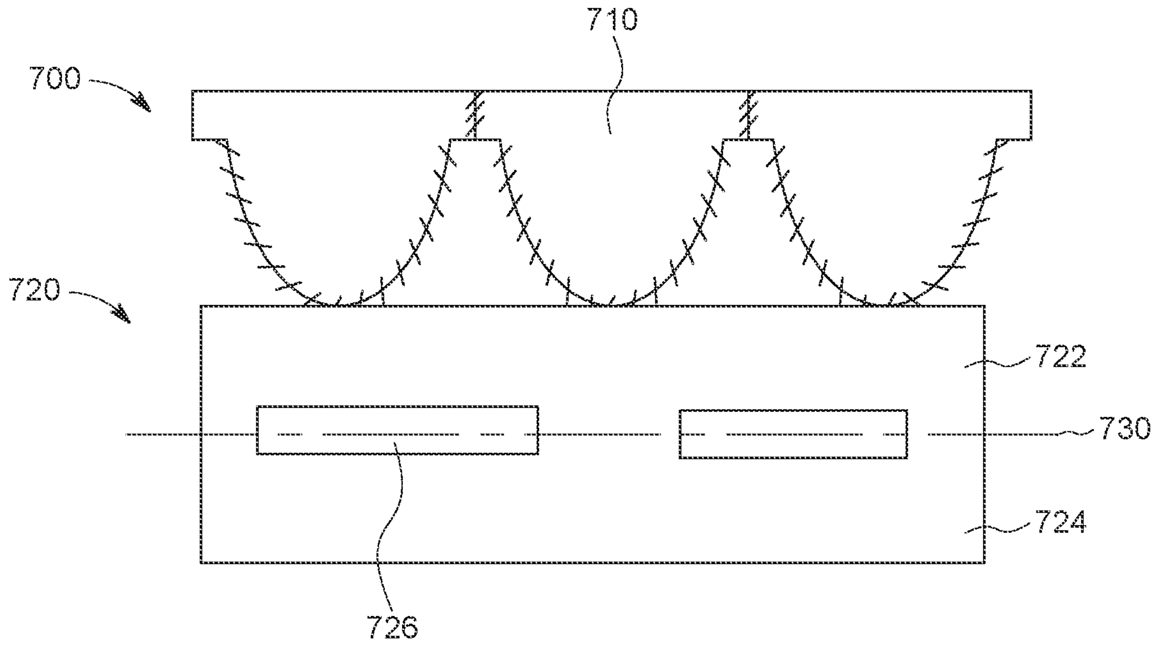
FIG. 6 illustrates a leaflet-cuff preassembly according to another aspect of the disclosure.

FIG. 6 illustrates a valve assembly 700 according to another aspect of the disclosure. FIG. 6 illustrates the valve assembly 700 including three leaflets 710 that are preassembled to each other and to a cuff 720 in a similar fashion as described in connection with FIG. 3. However, it should be understood that the leaflets 710 need not be preassembled to the cuff 720, and rather may be assembled to the cuff 720 and/or to each other only after the cuff 720 is coupled to the stent (not shown). It should also be understood that the leaflets 710 shown in FIG. 6 are not shown to scale relative to the cuff 720.

The cuff 720 may be generally rectangular, although other shapes may be suitable. Prior to coupling the cuff 720 to the stent, for example while the cuff 720 is laid flat on a table, the cuff 720 may be substantially symmetrical about a fold line 730. The fold line 730, which may be an imaginary line prior to assembly of the cuff 720 to the stent, may separate the cuff 720 into a first portion 722 which will form an inner cuff portion and a second portion 724 which will form an outer cuff portion. One or more openings or apertures 726 may be formed along the fold line 730. Although two apertures 726 are shown, it may be preferable for there to be one aperture 726 for each CAF of the stent (and/or for each leaflet 710). In order to assemble the valve assembly 700 to the stent, the fold line 730 may be generally positioned adjacent the outflow edge of the stent (such as the stent 602 of FIG. 5), and the apertures 726 aligned so that each CAF of the stent is aligned with a corresponding aperture 726 (or a portion of an aperture). The CAFs may be positioned so they pass through the corresponding aperture 726 (or a portion of the aperture), and the cuff 720 may be folded about fold line 730 so that the first cuff portion 722 confronts the luminal surface of the stent and the second cuff portion 724 confront the abluminal surface of the stent. The cuff 700 may then be coupled to the stent, for example via a single suture line that couples the inflow edge of the first cuff portion 722 (toward the top of the cuff in the view of FIG. 6) to the inflow edge of the second cuff portion 724 (toward the bottom of the cuff in the view of FIG. 6) and to the stent sandwiched between the two cuff portions. The outflow end of the cuff 720, which is generally around the fold line 730, may remain not directly coupled to the stent. In other embodiments, however, part or all of the outflow end of the cuff 720 may be directly coupled to the stent. If the leaflets 710 are not preassembled to the cuff 720, the leaflets 710 may be coupled to the stent after the cuff 720 is assembled and coupled to the stent. If the leaflets 710 are preassembled to the cuff 720, the leaflets 710 may be coupled (e.g., via suturing) to the first cuff portion 722 (e.g., after folding the leaflets 710 about the inflow edge of the first cuff portion 722 at the points where the leaflets 710 couple to the first cuff portion 722) along the attachment edges of the leaflets. This step may be performed either before or after coupling the cuff 720 to the stent. After the cuff 720 is draped over the outflow edge of the stent (e.g., similar to a poncho), the side edges of the cuff 720 may be coupled to each other, similar to as described in connection with FIG. 3. In some embodiments, it may be preferable for the apertures 726 to closely fit the size of the CAFs. However, in other embodiments, it may be preferable to intentionally oversize the apertures 726 relative to the CAFs. By oversizing the apertures 726 relative to the CAFs, space may be created so that retrograde blood flow may easily flow into the space between the inner cuff portion 722 and the outer cuff portion 724 via openings 726, with that blood flow tending to push the outer cuff portion 724 outwardly into engagement with the native valve annulus to mitigate PV leak. For example, the portions of the cuff(s) nearest the inflow end will be sealed (e.g. sutured) together. Since the apertures allow blood to flow into the region between the cuff(s) near the outflow end, the blood flowing into the space between the cuff(s) will tend to distend the cuff(s) at locations that are not tightly attached to a rigid structure (e.g. the frame). In this context, oversizing may refer to the apertures 726 being wider in the circumferential direction relative to the CAFs, longer in the axial direction relative to the CAFs, or both.

Figure 7:
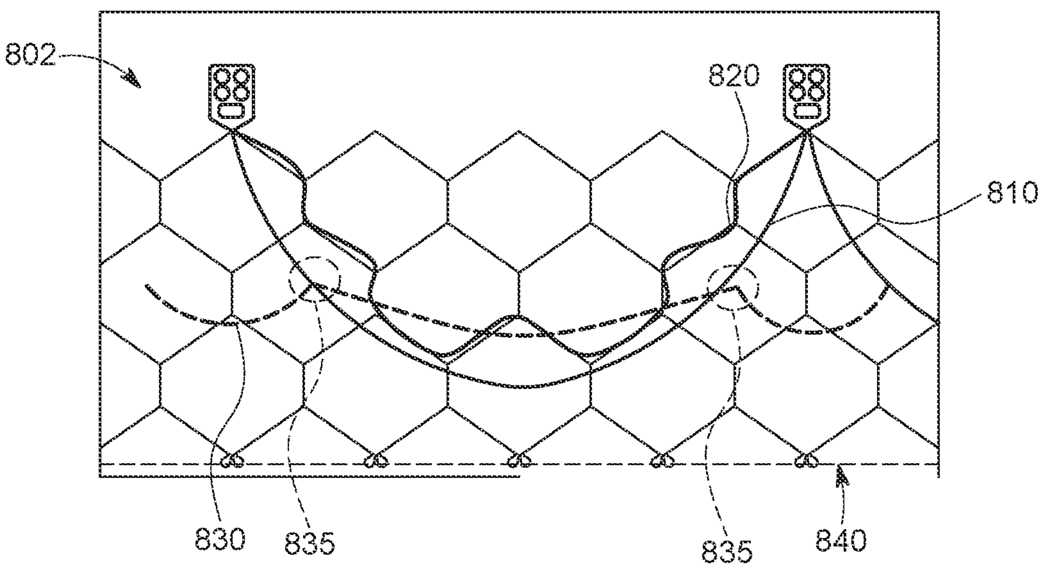
FIG. 7 is a highly schematic view of a valve assembly coupled to a stent according to another aspect of the disclosure.

FIG. 7 illustrates another aspect of the disclosure, with a stent 802 that is identical to stent 502. It should be understood that stent 802, along with stents 502 and 602, is illustrated as if cut longitudinally and laid flat on a table. In use, these stents are typically integrally formed as a continuous circular or cylindrical tube. The embodiment shown in FIG. 7 may be generally similar to that shown in FIG. 4, with certain important differences. For example, although the leaflet attachment line 810 has the same contour as shown in FIG. 4, in FIG. 7 the leaflet is attached to the cuff only after the cuff is attached to the stent 802. In use, the cuff may be a single structure and a first portion may be coupled to the luminal surface of the stent 802 along inner cuff attachment line 820 in the same manner as described in connection with FIG. 4. The relationship between leaflet attachment line 810 and inner cuff attachment line 820 may be the same as their counterparts described in connection with FIG. 4. After the cuff is attached along inner cuff attachment line 820, the cuff may be folded over the inflow edge of the stent 802 about fold line 840, in substantially the same manner as described in connection with FIG. 4. One main difference between FIGS. 4 and 7 is that, after the cuff is folded about fold line 840, the leaflets may be attached (e.g., via sutures) to the inner cuff and/or stent 820 along leaflet attachment line 810, with certain ones of the sutures (or stitches of the suture) also attaching to the outer cuff at select locations 835 along the contour of the outflow edge 830 of the outer cuff portion. These select locations 835 are shown in dashed circles in FIG. 7. One benefit of this assembly method and configuration is that additional sutures are not needed to attach the outer cuff to the stent 802 and/or inner cuff. This is because certain ones of the sutures or stitches that are already being used for the leaflet attachment line 810 are also serving to secure the outflow edge of the outer cuff. This results in fewer sutures, reducing complexity of assembly and also reducing the material bulk of the assembled prosthetic heart valve.

Figure 8:
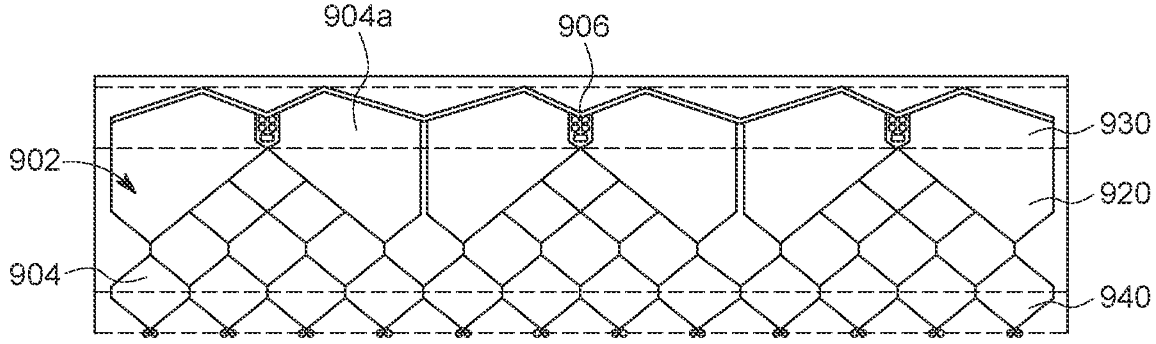
FIG. 8 is a highly schematic view of a cuff coupled to a stent via double folds according to another aspect of the disclosure.

While the embodiments described in connection with FIGS. 5-7 generally include a cuff that has a single fold to create inner and outer cuff portions, in some embodiments, more than one fold may be used. For example, FIG. 8 shows an example of a stent 902 that includes a plurality of rows of diamond-shaped and/or hexagonal cells 904, with large cells 904*a* extending between adjacent pairs of CAFs 906. It should be understood that the concepts described in connection with FIG. 8 may be used with stents having other shapes and configurations than stent 902, and other stents shown and described herein may be replaced by a stent similar to stent 902. A cuff 920 may be positioned to cover the entire interior or luminal surface of the stent 902, with excess material of cuff 920 extending beyond both inflow and outflow ends of the stent 902. That excess material may be folded over both the inflow end and outflow ends of the stent 902 to create a first upper (or outflow) outer cuff portion 930, and a second (or inflow) outer cuff portion 940. In some embodiments, the cuff 920 may be provided as a continuous tube with the ends folded over the terminal edges of the stent 902. In other embodiments, the cuff 920 may be provided as a flat piece (e.g., rectangular), with the side edges attached to each other. Either way, the cuff 920 may be coupled to stent 902 at only certain desired locations. For example, the first outer cuff portion 930 may be coupled to the CAFs 906 with sutures, for example tack stitches. The second outer cuff portion 940 may be attached to the stent 902 only at locations where two circumferentially adjacent cells 904 in the same row meet. With this configuration, blood may flow into space between the inner cuff and the outer cuff portions, particularly the second outer cuff portion 940, to help prevent PV leak. With the configuration described above, the top and bottom folds of the cuff 920 will hold the cuff 920 to the frame, with additional securement via stitches in selected locations. The leaflets may be coupled to the cuff 920 (e.g., via sutures) after the cuff 920 is coupled to the stent 902, or otherwise the leaflets may be provided preassembled to the cuff 920 as described in connection with embodiments above. In either case, significant amounts of suture material to attach the cuff 920 to the stent 902 may be avoided, resulting in relatively little bulk in the prosthetic heart valve due to suture material. This may also result in faster and less complex assembly of the valve assembly.

Figure 9:
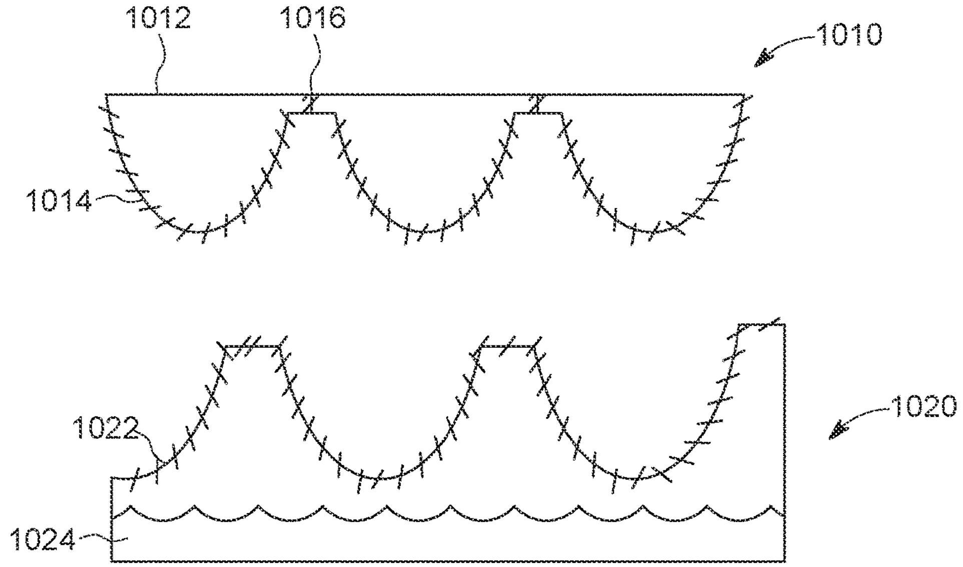
FIG. 9 is a highly schematic view of an inner cuff portion and an outer cuff portion of a valve assembly in a disassembled state.

FIG. 9 illustrates another cuff assembly according to an aspect of the disclosure. The cuff assembly of FIG. 9 is configured for use with a three-leaflet valve, but it should be understood that modifications may be made for use with a prosthetic valve having more or fewer than three leaflets. The cuff assembly of FIG. 9 includes an inner cuff 1010, and an outer cuff 1020. The inner cuff 1010 may have a shape that substantially replicates the shape of three coupled leaflets, similar to the leaflets 410 of FIG. 3. For example, the inner cuff 1010 may include a relatively straight outflow edge 1012, and a scalloped inflow edge 1014, which may be a sequence of three generally parabolic sections, each pair of adjacent parabolic sections separated by a connector 1016. The straight outflow edge 1012 may generally correspond to the free edges of the leaflets (e.g., free edges 412 of leaflets 410 in FIG. 3) and the scalloped inflow edge 1014 may generally correspond to the attached edges of the leaflets (e.g., attached edges 414 of leaflets 410 in FIG. 3). Although not shown, leaflets generally similar in shape to leaflets 410 may be positioned interior to the inner cuff 1010 and aligned with the corresponding contours of the inner cuff 1010.

The outer cuff 1020 may include an outflow edge 1022 with a complementary shape to the inner cuff 1010. For example, the outflow edge 1022 may be scalloped with three parabolic troughs, each pair of adjacent troughs separated by a peak. The outer cuff 1020 may also include a PV leak feature 1024 which may include a small strip of additional cuff material positioned radially outward of the inflow end of the outer cuff 1020, so that open space is created between the outer cuff and the PV leak feature 1024. As with other embodiments herein, retrograde blood flow may enter the space between the PV leak feature 1024 and the outer cuff 1020 to cause the PV leak feature 1024 to billow outwardly into sealing contact with the native valve annulus. For example, PV leak feature 1024 may have an outflow edge that is connected to the outer cuff 1020 at spaced locations so that openings are created between the connection locations, but the inflow edge of the PV leak feature 1024 may create a seal with the outer cuff 1020 so that blood entering the space between the PV leak feature 1024 and the outer cuff 1020 gets trapped within the PV leak feature 1024 and/or forces the PV leak feature 1024 to billow outwardly.

Although the inner cuff 1010 and outer cuff 1020 are shown spaced apart in FIG. 9, upon assembly to the stent, the inner cuff 1010 and outer cuff 1020 may be closely positioned to one another, with the scalloped inflow edge 1014 of the inner cuff 1010 aligned with the complementarily shaped troughs of the outflow edge 1022 of the outer cuff 1020. It should be understood that although the inner cuff 1010 may be aligned with the complementary shapes of the outer cuff 1020, the stent will be positioned between the inner cuff 1010 and outer cuff 1020. However, there will be little or no radial overlap between the inner cuff 1010 and the outer cuff 1020 upon assembly of the prosthetic heart valve. With this configuration, there is relatively little bulk in the prosthetic heart valve because there is no overlap (or no significant overlap) between the inner cuff and outer cuff. Rather, the close complementary shapes provide for a sealing zone that extends the entire axial length of the combined inner cuff 1010 and outer cuff 1020, while minimizing the amount of material required to create the desired seal, and maintaining abrasion resistance by providing a non-metal surface (e.g., the inner surface of the inner cuff 1010) that the leaflets may contact when opening. It should be understood that the hashed lines in FIG. 9 represent where stitches of a suture line may be present after assembling the inner cuff 1010 and outer cuff 1020 to a stent, with the sutures coupling the scalloped edges of the inner cuff 1010 to the scalloped troughs of the outer cuff 1020.

Figure 10:
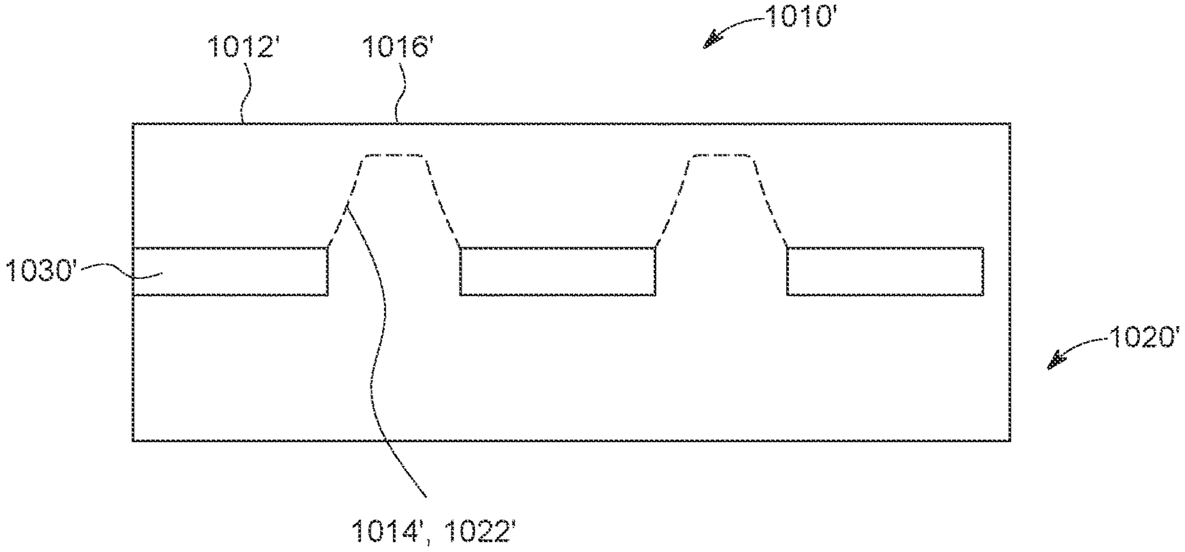
FIG. 10 is a highly schematic view of an alternate embodiment of the valve assembly of FIG. 9.

FIG. 10 illustrates an alternate embodiment of the valve assembly of FIG. 9. The inner cuff 1010' and outer cuff 1020' of FIG. 10 may be identical to the corresponding components of FIG. 9, with certain differences. For example, inner cuff 1010' may include three portions that generally correspond to the shape of leaflets, with each portion having a substantially straight outflow edge 1012' connected to an adjacent portion via a tab or connector 1016'. Similarly, the inner cuff 1010' may include a scalloped inflow edge 1014' that generally matches the scalloped trough 1022' of the outflow edge of the outer cuff 1020'. However, the main difference is that, instead of the inflow portion of the inner cuff 1010' and outflow portion of the outer cuff 1020' having very close alignment along their entire lengths, the alignment is intentionally interrupted to create gaps or openings

1030'. The openings 1030' may be positioned between adjacent peaks of the outer cuff 1020'. It should be understood that the leaflets (not shown) positioned inside the inner cuff 1010' would have the belly suture (e.g., the suture line along the attachment edge 414) extend below the aperture 1030'. With this embodiment, the cutouts or openings 1030' open to the belly of the leaflets inside the inner cuff 1010'. Thus, while the valve assembly of FIG. 10 has generally the same benefits as those described above in connection with FIG. 9, the openings 1030' allow an additional benefit. In particular, when the leaflets are in the closed or coapted portion, blood leaking around the outside of the stent (e.g., PV leak) may pass through the openings 1030' and act to help close the leaflets, since the openings 1030' lead to the leaflet bellies.

As with the valve assembly of FIG. 9, the valve assembly of FIG. 10, once assembled, would include the inner cuff 1010' positioned on the luminal surface of the stent and the outer cuff 1020' positioned on the abluminal surface of the stent. In the illustrated embodiment, one opening 1030' is provided for each leaflet. Although the openings 1030' are shown as generally rectangular, it should be understood that other shapes may be suitable to provide the same or similar functionality. Also, while a particular size for each opening 1030' is shown, it should be understood that the openings 1030' may be larger or smaller than shown to provide for a greater or smaller area through which retrograde blood flow may pass to further assist in closing the leaflets. In all embodiments, it is preferable that the opening 1030' is exclusively positioned above (in the outflow direction, or toward the top of the page in the view of FIG. 10) the suture line that attaches the leaflets (not shown) to the inner cuff 1010' and/or outer cuff 1020'. In order to create the openings 1030' the scalloped inflow edge 1014' of the inner cuff 1010' may be flattened relative to the embodiment shown in FIG. 9 and/or the scalloped trough of the outflow edge 1022' of the outer cuff 1020' may be provided with a different shape compared to the embodiment shown in FIG. 9. Also, although not shown in FIG. 10, outer cuff 1020' may include an additional PV leak mitigation feature such as PV leak feature 1024 shown in FIG. 9.

Figure 11:
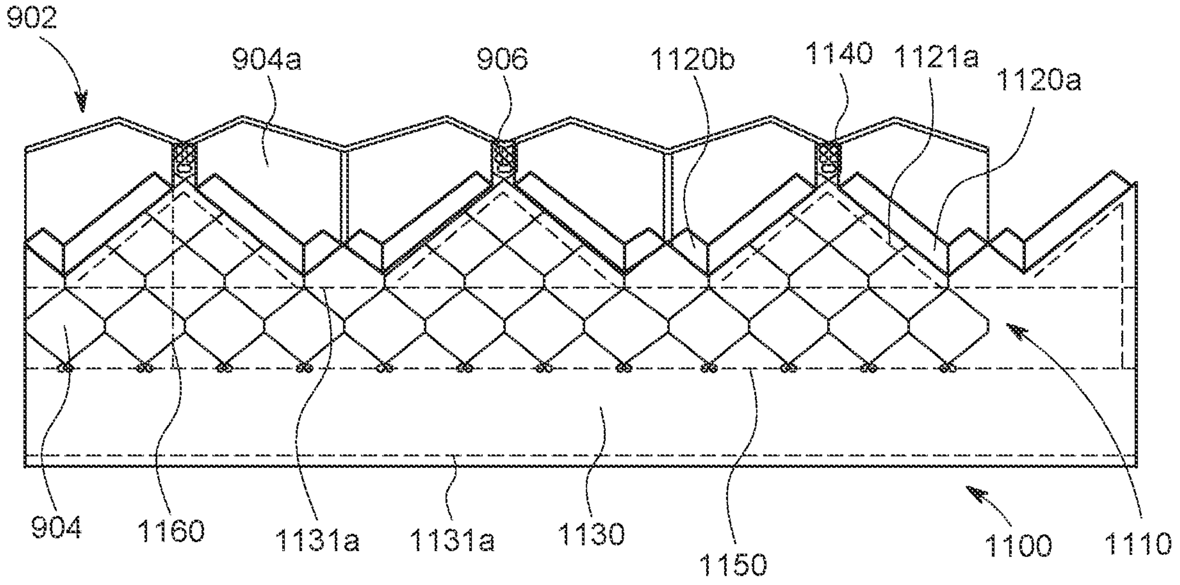
FIG. 11 is a highly schematic view of a profiled cuff overlying a stent prior to assembly according to another aspect of the disclosure.

FIG. 11 shows another embodiment of a cuff of a valve assembly. In particular, FIG. 11 illustrates a stent of a prosthetic heart valve if the stent were cut longitudinally and laid out flat on a table. The stent shown in FIG. 11 may be identical to stent 902 shown in FIG. 8, but it should be understood that the features described in connection with FIG. 11 may be modified to suit other stent designs. FIG. 11 also illustrates a cuff 1100 laid out flat over stent 902 and prior to attachment to the stent 902. Cuff 1100 may include a main body portion 1110 and a plurality of flaps or tabs along the outflow portion of the main body 1110. Each tab 1120*a*, 1120*b* may be precut and may extend a desired distance beyond a corresponding strut (or sequence of struts) that generally form a lower or inflow side of large cells 904*a*. When the cuff 1100 is aligned with the stent 902, the main body 1110 of the cuff 1100 covers all of the inner surfaces of the cells 904, with the tabs 1120 extending beyond the cells 904 into the large cells 904*a*. A cuff extension 1130 may extend beyond the bottom (or inflow end) of the stent 902, and CAF tabs 1140 may be generally aligned with CAFs 906. CAF tabs 1140 may have a generally rectangular shape and may be generally shaped to match the shape of the CAFs 906.

With the cuff 1100 overlaying the stent 902 as generally shown in FIG. 11, the tabs 1120*a*, 1120*b* may be folded over the struts separating the large cells 904*a* from the other cells 904 so that the tabs are positioned on the abluminal surface of the stent 902, and a running stitch (shown as a dashed line in FIG. 11) may be passed through the tabs 1120*a*, 1120*b* on the abluminal surface of the stent 902 and through the main body 1110 in the luminal surface of the stent 902 to secure the outflow edge of the cuff 1100 to the stent 902. In particular, large tabs 1120*a*, which in this embodiment follow about three cells 904, may be secured via running stitch 1121*a*. The smaller tabs 1120*b*, which may fold over a strut of only a single cell 904, may be coupled via a different running stitch, described below. The CAF tabs 1140 may be secured to CAFs 906 via sutures passing through the holes performed in the CAFs 906.

As noted above, the cuff includes an extension 1130 that extends a distance beyond the inflow edge of the stent 902. The extension 1130 may be folded over the inflow edge of the stent 906 so that the extension 1130 is on the abluminal surface of the stent 902. After folding over, a running stitch 1131*a* may be passed through the extension 1130 (on the abluminal surface of the stent 920) near the edge thereof and through the main body 1110 of the cuff (on the luminal surface of the stent) along a generally horizontal running stitch 1131*a*. It should be understood that, although two horizontal running stitch lines 1131*a* are shown in FIG. 11, the second running stitch line 1131*a* shown on cuff extension 1130 is only intended to show where the running stitch line 1131*a* is positioned on the cuff extension 1130. In practice, the location of the top and bottom running stitch lines 1131*a* in FIG. 11 overlap after the cuff extension 1130 is folded over the inflow edge of the stent 902, and both running stitch lines 1131*a* represent only a single physical running stitch. The horizontal running stitch line 1131*a* may additionally secure the small tabs 1120*b* to the main body 1110 of the cuff after the small tabs 1120*b* are folded over the outflow edge of the corresponding cells 904. In some embodiments, the horizontal running stitch line 1131*a* may create or otherwise allow for openings between the main body 1110 and the folded cuff extension 1130 so that retrograde blood may flow through those openings and cause the cuff extension 1130 to billow outwardly relative to the main body 1110. This billowing may provide increased sealing against PV leak.

After the extension 1130 is folded over the inflow edge of the stent 902, a bottom running stitch 1150 may be created along or adjacent to the fold to secure the inner and outer layers of the cuff 1100 at the inflow edge of the stent 902. In some embodiments, bottom running stitch 1150 may be omitted. However, bottom running stitch 1150 may help avoid the fabric from billowing inwardly toward the inner diameter of the valve. Because the stent 902 is typically formed as an integral tube member, and the cuff 1100 is typically formed as a flat sheet that is then wrapped into a tube shape, a vertical running stitch 1160 may be provided to couple the two side edges of the cuff 1100 when the cuff is positioned within the tubular stent 902. It should be understood that only a single vertical running stitch 1160 is contemplated in FIG. 11. The vertical stitch shown on the right side of FIG. 11 represents the same running stitch labeled 1160. In other words, the material of cuff 1100 extending beyond the right side of the stent 902 in FIG. 11 is the same as the material of cuff 1100 to the left of the labeled vertical running stitch 1160.

One of the benefits of the profiled cuff 1100 shown in FIG. 11 is that the various tabs 1120*a*, 1120*b* may provide for highly repeatable and accurate positioning of the cuff 1100 relative to the stent 902, which may allow for the valve assembly to be highly uniform over different actual products assembled according to the configuration shown and described in connection with FIG. 11, with little variability during the manufacturing process. Further, cuffs are typically coupled to stents using whip stitches, but the configuration of FIG. 11 is particularly well suited for running stitches and may allow for the cuff to be coupled almost entirely only to the cuff, as opposed to the stent. One benefit of using running stitches instead of whip stitches is that running stitches may enable the use of pre-defined laser-cut suture holes within the fabric, which may significantly increase the accuracy and repeatability of the stitching, while reducing the amount of skill required to assembly the device. Although not shown in FIG. 11, it should be understood that a plurality of leaflets (three if stent 902 is used as part of the prosthetic heart valve) would be positioned interior to the cuff 1100 and attached to the cuff 1100 and/or stent 902 to complete the manufacture of the prosthetic heart valve.

Figure 12:
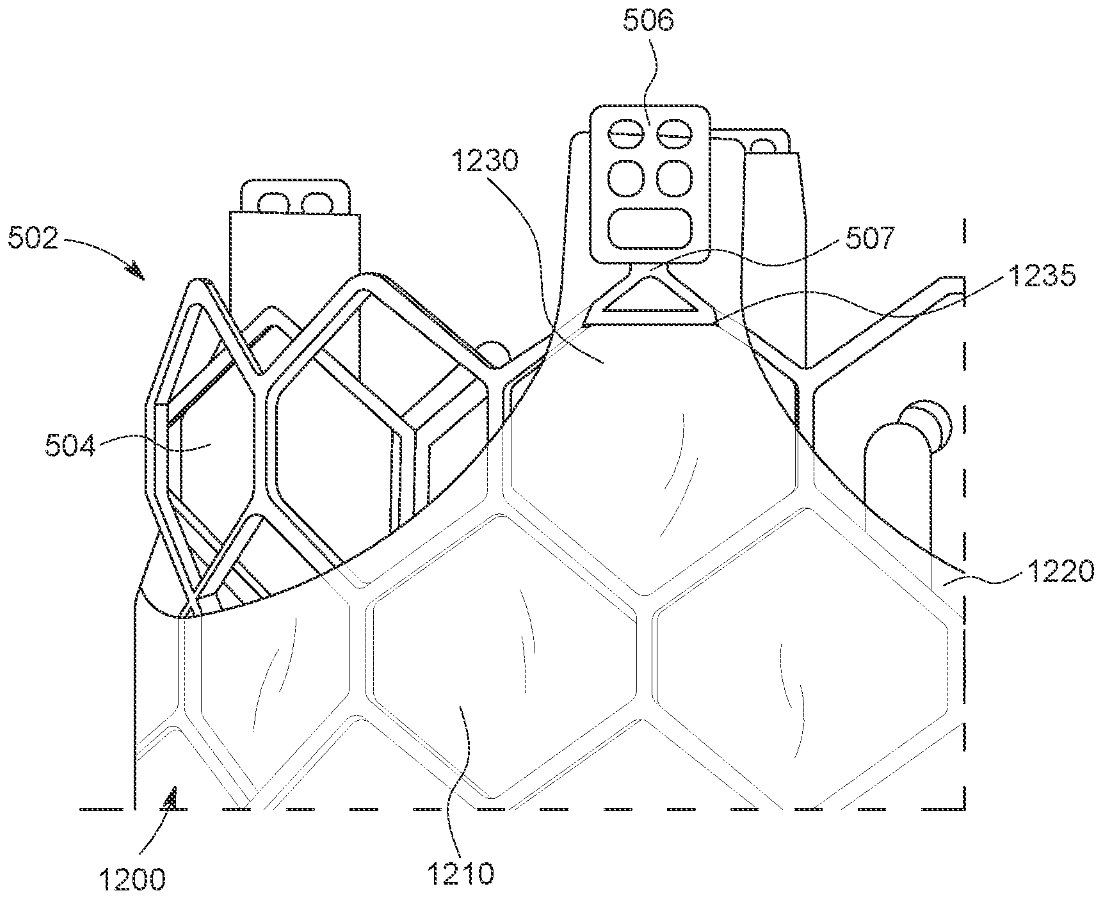
FIG. 12 shows a cuff with a slit through which a commissure attachment feature of the stent passes for securement.

FIG. 12 illustrates another cuff 1200 coupled to a stent that is the same as stent 502. FIG. 12 shows the stent 502 in an expanded state such that the stent is generally cylindrical in the form of a tube. In the embodiment shown in FIG. 12, cuff 1200 is positioned generally on the abluminal surface of the stent, with a main portion 1210 that extends to the inflow end of the stent 502 (not shown), three scalloped portions that form troughs 1220, and three peaks 1230 between each pair of circumferentially adjacent troughs 1220. Each peak 1230 may be formed with a generally horizontal slit 1235 formed therein. Each horizontal slit 1235 may have a width that extends most, but not all, of the width of the peak 1230. The width of the slit 1235 may be slightly greater than the width of each CAF 506 (the width being measured in the circumferential direction of the stent 502). To assemble the cuff 1200 to the stent 502, the three slits 1235 (in embodiments in which the prosthetic valve includes three leaflets and the stent 502 includes three CAFs 506) are alighted with the three CAFs 506, and the CAFs 506 are slipped through the slits 1235 as shown in FIG. 12. In some embodiments, buttonhole or similar stitching may be provided on the peak 1230 adjacent to the slit 1235 to provide reinforcement of the cuff 1200 at the slit 1235. Each peak 1230 may be attached to the corresponding CAF 506 via any suitable mechanism. For example, although more typical stitching may be used, the peaks 1230 may instead by coupled to the CAFs 506 via tying. For example, a single suture or similar material may be wrapped around a small width neck 507 of the CAF 506, pass through the peak 1230 and be knotted to complete the securement. Because the CAFs 506 passing through the slits 1235 may significantly stabilize the cuff 1200 relative to the stent 502, other portions of the cuff 1200 may be attached to the stent 502 using tying instead of typical suturing (e.g., whip stitching). For example, the cuff 1200 may be tied to the stent 502 at selected locations where adjacent cells 504 of the stent 502 meet. By allowing connection via tying instead of typical suturing, significantly less suture material may be used with the cuff 1200 of FIG. 12.

Although the cuff 1200 of FIG. 12 is shown as an exterior cuff, it should be understood that the cuff may instead be provided as an interior cuff. In other words, the outer cuff 1200 of FIG. 12 includes material that is substantially on the abluminal surface of the stent 502, except for the portions of the peaks 1230 that are positioned on the luminal surface of the CAFs 506 after the CAFs 506 are passed through the slits 1235. This configuration may be reversed, with the majority of the material of cuff 1200 on the luminal surface of the stent 502, except for the portions of the peaks 1230 that would be positioned on the abluminal surface of the CAFs 506 after the CAFs 506 are passed through the slits 1235. In addition, although FIG. 12 shows a stent 502 without a corresponding inner cuff, an inner cuff may additionally be provided, including in the style of FIGS. 9 and/or 10 described above. And as with other embodiments described herein, although prosthetic leaflets are not shown in FIG. 12, a plurality of prosthetic leaflets may be mounted to the cuff 1200 and/or the stent 502 to form the prosthetic heart valve.

Figure 13:
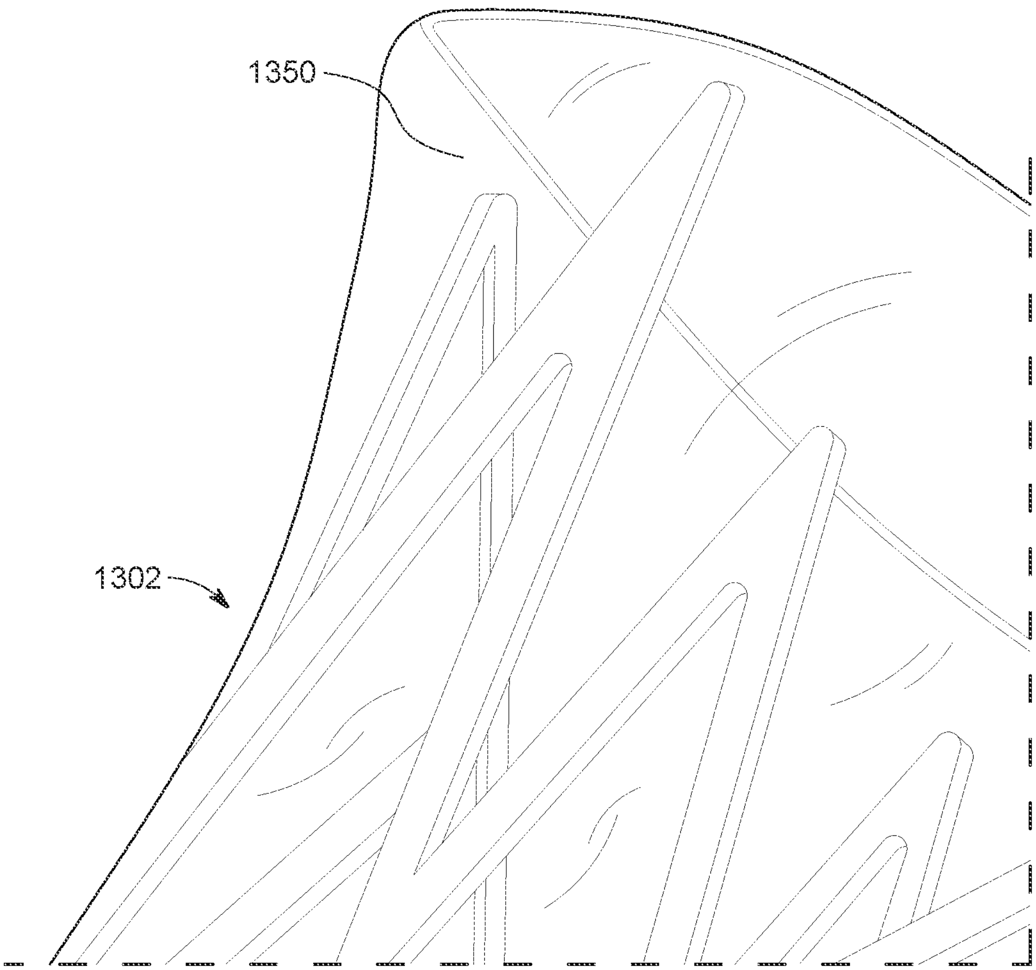
FIG. 13 illustrates a cuff formed by dip coating on a stent.

In some embodiments, a prosthetic heart valve may be formed with a polymer dipped or molded cuff that completely eliminates the need for suturing the cuff to the stent. For example, FIG. 13 illustrates a portion of an expanded stent 1302 which may be any of the stents described herein, or any other suitable stent for a prosthetic heart valve. The prosthetic heart valve also includes a polymer dipped or molded cuff 1350 that eliminates the need for suturing a fabric to the stent 1302. For example, the cuff 1350 may be provided as an integral combination of a base coating and a top coating that renders the stent 1302 circumferentially fluid-impermeable. Such integral coatings may have improved polymer adherence to the shape memory alloy stent. In one example, the polymeric coating generally provides a base coating formulation comprising one or more specialty multifunctional organosilane coupling compounds and other compounds, which form a thin siloxane polymer film, or siloxane monolayer directly on the metallic surfaces of the stent of a shape memory alloy. When this thin film or monolayer is dried and cured, it provides strong covalent bondability and adhesion to the metallic stent and some active molecular mechanism of adherence to another top layer, such as a top coating, that may be applied onto the base coating. The top coating may provide a flexible, and integral fluid-impermeable film circumferentially encapsulating the metallic stent 1302. Both the base coating and the top coating may be present on the coated substrate in one or more layers. Suitable polymer coatings are described in greater detail in International Patent Application Publication No. WO 2019/194956, the disclosure of which is hereby incorporated by reference herein.

In some embodiments, the cuff of the prosthetic heart valve may be provided as a fabric or polymer that is coupled to the stent via heat bonding to reduce or eliminate the amount of stitching necessary to couple the cuff to the stent. This alteration may be provided to any of the prosthetic heart valves described above. As one example, referring to the embodiment of FIG. 8, the folded-over outer cuff portions 930 and 940 may be coupled to the portion of the cuff 920 that remains on the interior of the stent via heat bonding. As another example, referring back to FIG. 11, after folding the tabs 1120*a*, 1120*b* to the exterior of the stent 902, the tabs 1120*a*, 1120*b* may be heat bonded to the portion of the cuff 1100 that remains on the interior of the stent. Still referring to FIG. 11, the cuff extension 1130 may be similarly heat bonded to the portion of the cuff 1100 that remains on the interior of the stent. In other embodiments, any of the inner cuffs (or inner cuff portions) described herein may be heat bonded to their complementary outer cuffs (or outer cuff portions) instead of being fastened via sutures or other means. By heat bonding the cuff to itself, sutures may be mostly or entirely omitted, for example because the cuff is no longer being directly connected to the stent. By reducing or eliminating the use of sutures to couple the cuff to the stent, the manufacturing process may be simpler and the resulting prosthetic heart valve may have less bulk and thus be able to achieve a smaller crimp profile.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of manufacturing a prosthetic heart valve, the method comprising:

coupling a plurality of prosthetic leaflets to each other, each of the plurality of leaflets having a free edge and a scalloped edge;

coupling a portion of the scalloped edge of each of the plurality of prosthetic leaflets at spaced apart locations to a straight first edge of a cuff, to form a valve assembly;

positioning the plurality of prosthetic leaflets on the luminal side of a stent and wrapping the cuff around an inflow edge of the stent so that at least a portion of the cuff is positioned on the abluminal side of the stent; and coupling the valve assembly to the stent to form the prosthetic heart valve;

wherein the valve assembly is formed prior to the plurality of prosthetic leaflets being coupled to the stent and prior to the cuff being coupled to the stent.

2. The method of claim 1, wherein upon forming the valve assembly, the valve assembly is in a flat condition.

3. The method of claim 1, wherein each of the plurality of prosthetic leaflets includes tabs between the free edge and the scalloped edge.

4. The method of claim 1, wherein coupling the valve assembly to the stent includes coupling the cuff to a luminal surface of the stent so that an extended portion of the cuff extends beyond an inflow edge of the stent and wrapping the extended portion of the cuff around the inflow edge of the stent so that the extended portion of the cuff is positioned on an abluminal surface of the stent.

5. The method of claim 1, wherein forming the valve assembly includes coupling a terminal edge of the cuff to the stent at spaced apart locations along the terminal edge of the cuff after wrapping the cuff around the inflow edge of the stent.

6. The method of claim 1, wherein the scalloped edge of each of the plurality of prosthetic leaflets is sutured through the stent to the cuff.

7. The method of claim 1, wherein the cuff is wrapped around the inflow edge of the stent so that the straight edge of the cuff is positioned adjacent the inflow edge of the stent.

* * * * *